US007595192B2

(12) United States Patent
Goletz et al.

(10) Patent No.: US 7,595,192 B2
(45) Date of Patent: Sep. 29, 2009

(54) PROCESS FOR THE PRODUCTION OF TEMPERATURE-INDUCED TUMOR CELL LYSATES FOR USE AS IMMUNOGENIC COMPOUNDS

(75) Inventors: Steffen Goletz, Glienicke (DE); Hans Baumeister, Berlin (DE); Ute Schöber, Berlin (DE)

(73) Assignee: Glycotype GmbH, Berlin (DE)

( * ) Notice: Subject to any disclaimer, the term of this patent is extended or adjusted under 35 U.S.C. 154(b) by 0 days.

(21) Appl. No.: 10/524,738

(22) PCT Filed: Aug. 18, 2003

(86) PCT No.: PCT/EP03/09140

§ 371 (c)(1),
(2), (4) Date: Sep. 15, 2005

(87) PCT Pub. No.: WO2004/018659

PCT Pub. Date: Mar. 4, 2004

(65) Prior Publication Data

US 2006/0127419 A1   Jun. 15, 2006

(51) Int. Cl.
 *C12N 5/00* (2006.01)
(52) U.S. Cl. ..................................................... 435/325
(58) Field of Classification Search ..................... 514/1; 435/325
See application file for complete search history.

(56) References Cited

U.S. PATENT DOCUMENTS

| 4,931,275 | A | 6/1990 | Shinitzky et al. |
| 5,948,646 | A | 9/1999 | Srivastava |
| 5,961,979 | A | 10/1999 | Srivastava |
| 6,168,793 | B1 | 1/2001 | Srivastava |
| 6,984,384 | B1 * | 1/2006 | Subjeck et al. ........... 424/184.1 |
| 2006/0292129 | A1 | 12/2006 | Goletz et al. |

FOREIGN PATENT DOCUMENTS

| WO | WO 94/29469 | 12/1994 |
| WO | WO 97/00957 | 1/1997 |
| WO | WO 9740182 A | 10/1997 |
| WO | WO 99/29834 A | 6/1999 |
| WO | WO 03/023023 | 8/2001 |
| WO | WO 2004009632 A | 1/2004 |
| WO | WO 2004018659 A | 3/2004 |

OTHER PUBLICATIONS

Huang et al (Cancer Research, Jul. 1, 2000, 60:3435-3439).*
Gough et al (Cancer Research, 2001, 61:7240-7247).*
Samali et al (FEBS letters, Nov. 1999, 461(3):306-310).*
Mivechi (Cancer Research, Apr. 1989, 49: 1954-1958).*
Lozzio and Lozzio (Blood, Mar. 1975, 45(3): 321-334).*
Yoshima et al (JBC, Sep. 1998, 273(39): 25466-25471).*
PCT International Search Report.

Somersan S. et al., "Primary Tumor Tissue Lysates Are Enriched in Heat Shock Proteins and Induce the Maturation of Human Dendritic Cells," *Journal of Immunology*, vol. 167, No. 9, pp. 4844-4852 (2001).
Chen Z. et al., "Efficient Antitumor Immunity Derived From Muturation of Dendritic Cells That had Phagocytosed Apoptotic/Necrotic Tumor Cells," *International Journal of Cancer*, vol. 93, No. 4, pp. 539-548 (2001).
Kotera Y. et al., "Comparative Analysis of Necrotic and Apoptotic Tumor Cells as a Source of Antigen(s) in Dendritic Cell-Based Immunization," *Cancer Research*, vol. 61, No. 22, pp. 8105-8109 (2001).
Sauter Birthe et al., "Consequences of Cell Death: Exposure to Necrotic Tumor Cells, but Not Primary Tissue Cells or Apoptotic Cells, Induces the Maturation of Immunostimulatory Dendritic Cells," *Journal of Experimental Medicine*, vol. 191, No. 3, pp. 423-433 (2000).
Gough M.J. et al., "Macrophages Orchestrate the Immune Response to Tumor Cell Death," *Cancer Research 61*, pp. 7240-7247 (2001).
Albert, "Dendritic cells acquire antigen from apoptotic cells and induce class I-restricted CTLs," *Nature*, 392:86-89 (1998).
Allison A. et al., "The role of cytokines in the action of immunological adjuvants," *Vaccine Design The Role of Cytokine Networks*, Gregoriadis ed., NATO ASI Series A: Life Sciences, vol. 293, pp. 1-9, Plenum Press, NY (1997).
Berd, "Autologous hapten-modified melanoma vaccine as postsurgical adjuvant treatment after resection of nodal metastases," *J. Clin. Oncol.*, 15:2359-2370 (1997).
Berthier-Vergnes, "Induction of IgG Antibodies Directed to a $M_r$ 31,000 Melanoma Antigen in Patients Immunized with Vaccinia Virus Melanoma Oncolysates," *Cancer Res.* 54:2433-2439 (1994).
Binder, "Cutting Edge: Heat Shock Protein gp96 Induces Maturation and Migration of $CD11c^+$ Cells In Vivo," *J. Immunol.*, 165:6029-6035 (2000).
Bomford et al., "The control of the antibody isotype response to recombinant human immunodeficiency virus gp120 antigen by adjuvants," *AIDS Res. Hum. Retroviruses*, 8:1765 et seq. (1992).
Bourdon, "Inhibition of Tumoral Graft Growth by Pretreatment with Normal or Heat-modified Tumoral Cells," *Ann. Immunology* 1, 43-63 (1981).
Cao, "Immunodetection of epithelial mucin (MUC1, MUC3) and mucin-associated glycotopes (TF, Tn, and sialosyl-Tn) in benign and malignant lesions of colonic epithelium: apolar localization corresponds to malignant transformation," *Virchows Arch.*, 431:159-166 (1997).

(Continued)

*Primary Examiner*—Sean E Aeder
(74) *Attorney, Agent, or Firm*—Finnegan, Henderson, Farabow, Garrett & Dunner, LLP

(57) ABSTRACT

The present invention relates to a process for the production of an immunogenic compound comprising inducing necrosis by temperature in tumor cells and lysing said necrotic tumor cells so as to obtain a lysate. Furthermore, the invention provides a method for the production of a pharmaceutical composition. Additionally, the invention relates to a pharmaceutical composition comprising a lysate obtainable by the aforementioned process. Moreover, methods and uses for vaccination against cancers, tumorous diseases, infections and/or autoimmune diseases comprising administering the cell lysates of the invention or dendritic cells loaded with the cell lysate loaded to an individual are provided.

39 Claims, 7 Drawing Sheets

OTHER PUBLICATIONS

Figure 1:
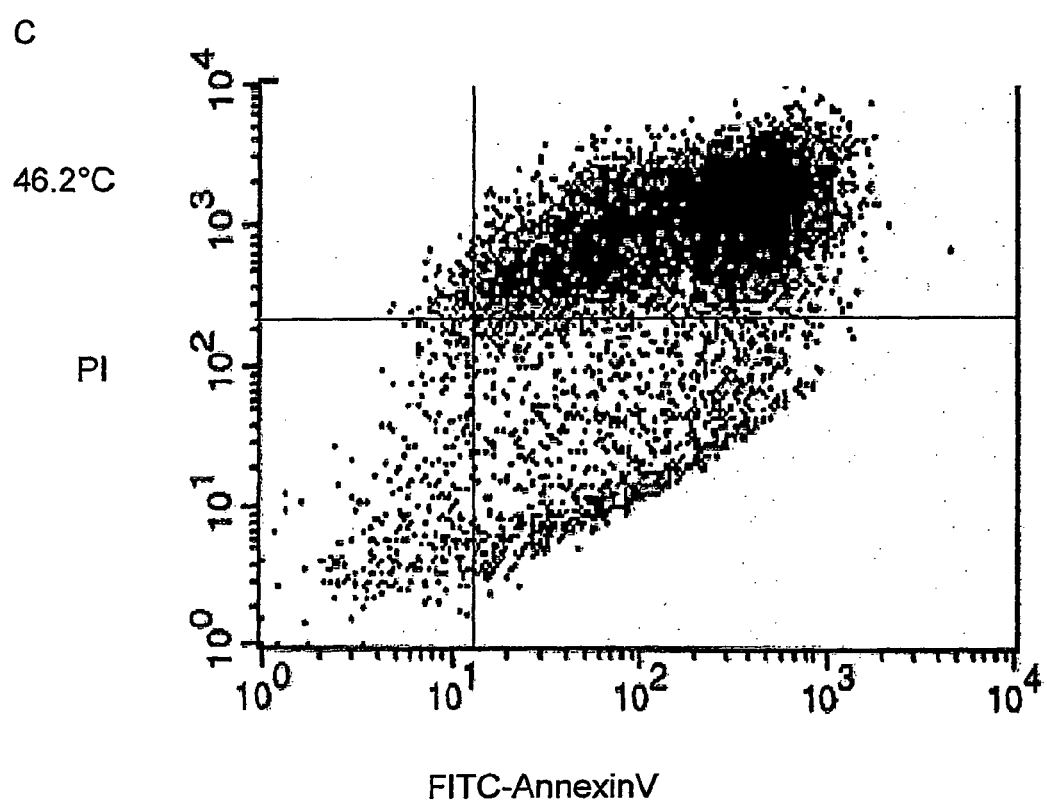
Figure 1:
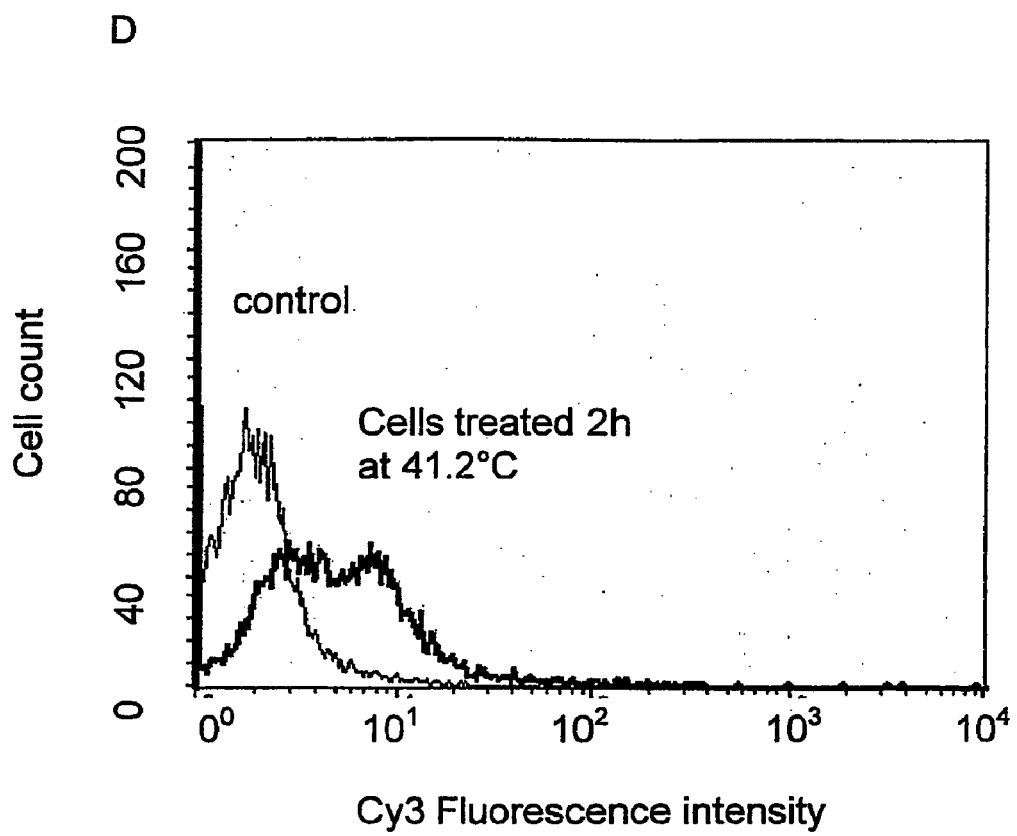

Cavaliere, "Selective heat sensitivity of cancer cells. Biochemical and clinical studies," *Cancer* 20:1351-1381 (1967).
Check, "Protection against transplanted and spontaneous lymphoma by inoculation of heat-altered syngeneic tumor cells in splenectomized mice," *Cancer*, 34:197-203 (1974).
Clayman (ed.), The American Medical Association Encyclopedia of Medicine at 573-574, 576 and 1034 (1989).
Cox et al., "Adjuvants—A classification and review of their modes of action," *Vaccine*, vol. 15, pp. 248 et seq., (1997).
Cox et al., "Development of an Influenza—ISCOM.TM. Vaccine," in *Vaccine Design* at pp. 33-49 (1997).
Cryz, Jr., S.J., *Immunotherapy and Vaccines*, edited by Stanley J. Cryz, pp. 3-11, VCH, Weinheim, Germany (1991).
Dickson, "Hyperthermia in the treatment of cancer," *Lancet*, 1:202-205 (1979).
*Dictionary of Immunology*, pp. 3, 7, 46, 87-88, 94, 97, 105, 116.
Dressel, "Heat Shock Protein 70 Is Able to Prevent Heat Shock-Induced Resistance of Target Cells to CTL," *J. Immunol.*, 164:2362-2371 (2000).
Feng, "Stressed apoptotic tumor cells express heat shock proteins and elicit tumor-specific immunity," *Blood*, 97:3505-3512 (2001).
Ferencik, M., *Handbook of Immunochemistry*, p. 115-116, Chapman & Hall (1993).
Fujiwara, "Establishment of a tumor-specific immunotherapy model utilizing TNP-reactive helper T cell activity and its application to the autochthonous tumor system," *J. Immunol.*, 133:509-514 (1984).
*Fundamental Immunology*, p. 1007-1009, Ed. W.E. Paul, Raven Press, NY.
Galluci, "*Danger signals: SOS to the immune system,*" *Curr. Opin. Immunol.*, 13:114-119 (2001).
Galluci, "Natural adjuvants: Endogenous activators of dendritic cells," *Nat. Med.*, 11:1249-1255 (1991).
Giovanella, "Effects of Elevated Temperatures and Drugs on the Viability of L1210 Leukemia Cells," *Cancer Res.*, 30:1623-1631 (1970).
Luftig, R.B., *Microbiology and Immunology*, pp. 228-229, Lippincott-Raven Pub, Phila. (1998).
Mach, "Cytokine-secreting tumor cell vaccines," *Curr. Opin. Immunol.* 12, 571-575 (2000).
Leffell, Mary S., An Overview of the Immune System: The Molecular Basis for Immune Responses, in *Human Immunology Handbook*, pp. 1-45.
Melcher, "Apoptosis or necrosis for tumor immunotherapy: what's in a name?" *J. Mol. Med*, 77:824-833 (1999).
Melcher, "Tumor immunogenicity is determined by the mechanism of cell death via induction of heat shock protein expression," *Nat. Med.*, 4:581-587 (1998).
Mise, "Effect of Heat Treatment on Tumor Cells and Antitumor Effector Cells," *Cancer Res.*, 50:6199-6202 (1990).
Mitchell, "Active Specific Immunotherapy for Melanoma: Phase I Trial of Allogeneic Lysates and a Novel Adjuvant," *Cancer Res.*, 48:5883-5893 (1988).
Mondovi, "Increased Immunogencity of Ehrlich ascites cells after heat treatment," *Cancer*, (30)4:885-888 (1972).
Peters et al., "Preparation of Immuno-Therapeutic Autologous Tumor Cell Vaccines from Solid Tumors," *Cancer Res.*, 39:1353-1360 (1979).
Phillips, T., *Analytical Techniques in Immunochemistry*, pp. 307-310, Marcel Dekker, NY (1992).
Price, "Effect of heat and glutaraldehyde upon the immunogenicity of Meth A sarcoma cells," *Br. J. Cancer* 40:663-665 (1979).
Restifo, "Building better vaccines: how apoptotoc cell death can induce inflammation and activate innate and adaptive immunity," *Curr. Opin. Immunol.*, 12:597-603 (2000).
Romani et al., "Proliferating dendritic cell progenitors in human blood," *J. Exp. Med.*, 180:83-93 (1994).
Schild, "gp96—the immune system's Swiss army knife," *Nat. Immunol.* 1:100-101 (2000).
Selawry, "Hyperthermia in Tissue-cultured Cells of Malignant Origin," *Cancer Res.*, 17:785-791 (1957).
Sensi, "Clonal Expansion of Lymphocytes in Human Metastases after Treatment With a Hapten-modified Autologous Tumor Vaccine,"*Clin. Invest.* 99:710-717 (1997).
Shaif-Muthana, "Dead or Alive: Immunogenicity of Human Melanoma Cells When Presented by Dendritic Cells," *Cancer Res.*, 60:6441-6447 (2000).
Sivanandham, *Biological Therapy of Cancer*, Ed. Rosenberg, S.A., 632-647 (2000).
Snippe et al., "Adjuvant Directed Immune Specificity at the Epitope Level. Implications for Vaccine Development. A Model Study Using Semliki Forest Virus Infection of Mice," pp. 155-166 in *Vaccine Design*.
Todryk, "Heat shock protein 70 induced during tumor cell killing induces Th1 cytokines and targets immature dendritic cell precursors to enhance antigen uptake," *The Journal of Immunology*, 163:1398-1408 (1999).
Vermes, "A novel assay for apoptosis. Flow cytometric detection of phosphatidylserine expression on early apoptotic cells using fluorescein labelled Annexin V," *J. Immunol. Meth.*, 184:39-51 (1995).
Wells, "Heat shock proteins, tumor immunogenicity and antigen presentation: an integrated view," *Immunol. Today*, 21:129-132 (2000).
Goletz, et al., "Thomsen-Friedenreich Antigen: the "hidden" tumor antigen," *Adv. Exp. Med. Biol.*, 535:147-62 (2003).
Agrawal, et al. "Cancer-associated MUC1 mucin inhibits human T-cell proliferation, which is reversible by IL-2.", *Naturel. Med.*, 4(1):43-9 (1998).
Anderson. "Human Gene Therapy". Science, vol. 256, pp. 808-813, (1992).
Böhm et al., "Carbohydrate Recognition on MUC1-Expressing Targets Enhances Cytoxicity of a T cell Subpopulation", *Scandinavian Journal of Immunology*, vol. 46, No. 1, pp. 27-34, XP-002323076 (1997).
Brummelkamp, et al. "A System for Stable Expression of Short Interfering RNAs in Mammalian Cells", Science, vol. 296, pp. 550-553, (2002).
Dall'Olio, et al., "Expression of beta-galactoside alpha 2,6-sialyltransferase does not alter the susceptibility of human colon cancer cells to NK-mediated cell lysis." *Glycobiology*, 7:507-513 (1997).
Duk et al., "Purification of Human Anti-TF (Thomsen-Friedenreich) and Anti-Tn Antibodies by Affinity Chromatography on Glycophorin A Derivatives and Characterization of the Antibodies by Microtiter Plate ELISA", *Archivum Immunologiae et Therapiae Experimentalis*, vol. 46, No. 2, pp. 69-77,, XP-008045186, (1998).
Elbashir, et al. "Duplexes of 21-nucleotide RNAs mediate RNA interference in cultured mammalian cells". Nature, vol. 411, pp. 494-498, (2001).
Gollasch et al., "Identification of Immunogenic Peptide-Mimics for the Thomsen-Friedenreich-Glycoantigen", *Annals of Hematology*, Berlin, DE, vol. 77, No. suppl. 2, p. S84, XP-000960533, (1998).
Ichiyama, "Induction of Non-HLA-restricted Anti-tumour Effector Cells with Strong Cytoxic Activity Using MUC1/B7 Cotransfected K562 Cells", *Cell Resource Center for Biomedical Research, Institute of Development, Aging, and Cancer, Tohoku University*, Sendai, Japan, vol. 51, No. 3-4, pp. 93-110, XP-001182213, (2000).
Isner, et al. "Clinical evidence of angiogenesis after arterial gene transfer of phVEGF165 in patient with ischaemic limb". The Lancet, vol. 348, pp. 370-374, (1996).
Karsten et al., "Enhanced Binding of Antibodies to the DTR Motif of MUC1 Tandem Repeat Peptide is Mediated by Site-Specific Glycosylation", *Cancer Research, American Association for Cancer Research*, Baltimore, MD, US, vol. 58, No. 12, pp. 2541-2549, XP-002112486, (Jun. 15, 1998).
Kunz, "Synthetic Glycopeptides for the Development of Tumour-selective Vaccines", *Journal of Peptide Science: an Official Publication of the European Peptide Society*, vol. 9, No. 9, pp. 563-573, XP-00845163, (Sep. 2003).
Natali, et al., *Heterogeneity in the expression of HLA and tumor-associated antigens by surgically removed and cultured breast carcinoma cells*. Cancer Res 1983; 43:660-668.
Novina, et al. "siRNA-directed inhibition of HIV-1 infection". Nature Medicine, vol. 8, No. 7, pp. 681-686, (2002).

Ohyama, et al. "Dual roles of sialyl Lewis X oligosaccharides in tumor metastasis and rejection by natural killer cells", The EMBO Journal, vol. 18, No. 6, pp. 1516-1525, (1999).

Ohyama, et al. "Natural killer cells attack tumor cells expressing high levels of sialyl Lewis x oligosaccharides". PNAS, vol. 99, No. 21, pp. 13789-13794., (2002).

Ouagari, et al. "Glycophorin A Protects K562 Cells from Natural Killer Cell Attack". The Journal of Biological Chemistry, vol. 270, No. 45, pp. 26970-26975, (1995).

Owens, et al. "Identification of two short internal ribosime entry sites selected from libraries of random oligonucleotides". PNAS, vol. 98, No. 4, pp. 1471-1476, (2001).

Paddison, et al. "Short hairpin RNAs (shRNAs) induced sequence-specific silencing in mammalian cells". Genes & Development, vol. 16, pp. 948-958, (2002).

Pahlsson, et al., "Biochemical characterization of the O-glycans on recombinant glycophorin a expressed in Chinese hamster ovary cells." *Glycoconj. J.*, 11:43-50 (1994).

Springer, et al., "Immunoreactive T and Tn epitopes in cancer diagnosis, prognosis, and immunotherapy." *J. Mol. Med.*, 75:594-602 (1997).

Sivanandham, et al. "Cancer Vaccines: Clinical Applications". Principles and Practice of the Biologic Therapy of Cancer, Third Edition, S. Rosenberg, pp. 632-647, Lippincott Williams & Wilkins, Philadelphia, PA., (2000).

Van Rinsum, et al., "Specific inhibition of human natural killer cell-mediated cytotoxicity by sialic acid and sialo-oligosaccharides." *Inc. J. Cancer*, 38:915-922 (1986).

Verma, et al. "Gene therapy—promises, problems and prospects". Nature, vol. 389, pp. 239-242, (1997).

Office action dated Jan. 27, 2009 from U.S. Appl. No. 10/568,098.

* cited by examiner

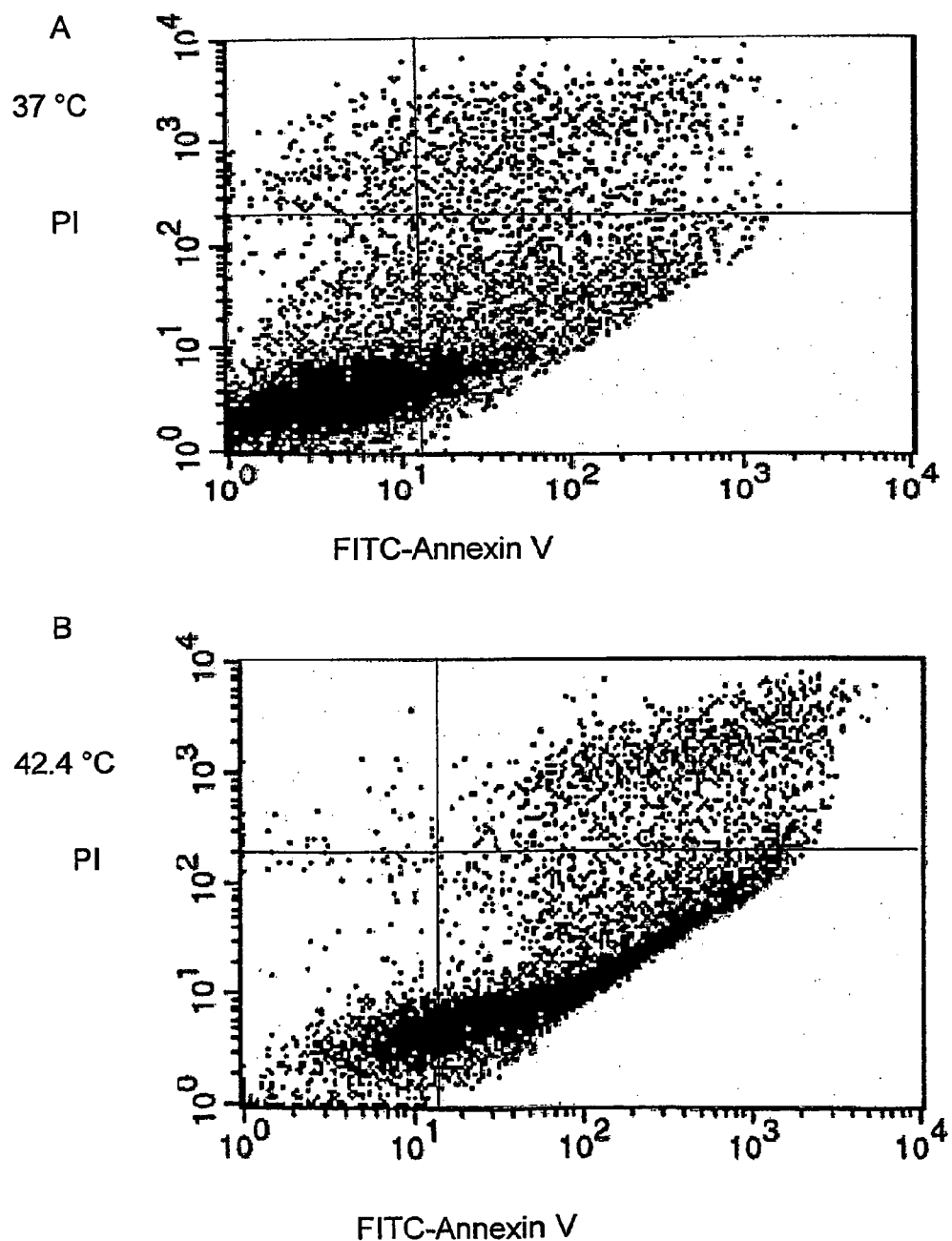
Figure 1 A, B
Analysis of propidium iodide and FITC-AnnexinV labelled temperature induced tumor cells A-C and anti-Hsp70 labeled NM-F9 tumor cells by flow cytometry

Detection of cellular Hsp 70 expression in temperature treated K562 tumor cells by immunocytochemical staining NM-F9 derived from K562 cells incubated at 41.2°C Hsp 70 positive NM-F9
cells stained with secondary
Cy3-labelled antibody NM-F9 derived from K562 cells incubated at 46.2°C Dark field control Hsp 70 positive NM-F9 cells
stained with secondary
Cy3-labelled antibody In vitro analysis of T cell stimulation by temperature treated NM-F9 tumor cell lysate loaded dendritic cells

In vitro Induction of CD8+ T-cell responses with various necrotic NM-F9 cell lysates (after 1 Stimulation)

Necrotic NM-F9 lysates:

A) 2h 46.5 °C
B) 3h 46.5 °C
C) 2h 46.5 °C +
    3h 37.0 °C
D) 3h 46.5 °C +
    3h 37.0 °C
E) 2h 46.5 °C +
    22 h 37 °C
F) 2h 46.5 °C +
    22 h 37 °C

PROCESS FOR THE PRODUCTION OF TEMPERATURE-INDUCED TUMOR CELL LYSATES FOR USE AS IMMUNOGENIC COMPOUNDS

The present invention relates to a process for the production of an immunogenic compound comprising inducing necrosis in tumor cells and by increasing the temperature of the cells and lysing said necrotic tumor cells so as to obtain a lysate. Furthermore, the invention provides a method for the production of a pharmaceutical composition. Additionally, the invention relates to a pharmaceutical composition comprising a lysate obtainable by the aforementioned process. Moreover, methods and uses for vaccination against cancers, tumorous diseases, infections and/or autoimmune diseases comprising administering the cell lysates of the invention or dendritic cells loaded with the cell lysate loaded to an individual are provided.

Vaccination involves the administration of an agent to an individual, which will stimulate the immune system to react against the "foreign" components of the vaccine. The vaccine can be administered, inter alia, into the skin, muscle, intraorally, subcutaneous, intradermally, intranodally, intraperitoneally, intra- or peritumorally or intravenously. The foreign components of the vaccine are known as "antigens". As a result of a vaccination procedure an individual develops immunity so that a subsequent exposure to the antigen(s) will evoke a response to eliminate or destroy the antigen carrying cells, organisms or particles or improve the disease symptoms or protect from a connected disease. Vaccines have been highly effective in protecting people from infectious organisms. Vaccinations for bacterial and viral infectious agents are now routinely used for: influenza viruses, measles, chicken pox, polio, pneumococcal bacteria, and hepatitis viruses and the like.

Because of the success in immunizing individuals against certain infectious organisms, it has been a great task of clinicians and scientists to develop effective vaccines against cancers.

The fight against infectious diseases with vaccines also teaches that prevention of infectious diseases with vaccines is easier than therapy of the same disease under development. This experience has been interpreted as suggesting that prophylactic vaccination against cancer may be more successful than vaccination when the disease is at an advanced stage. Therefore, several different types of cancer vaccines or immune therapies are under development and are aimed to be used for preventing, ameliorating and/or treating cancer and/or tumorous diseases.

In principle, the assumption of the foregoing was the following: tumor cells can be weakened, or attenuated, and injected like a vaccine into a mammal, e.g. a mouse. Afterwards, if these same tumor cells, at full strength, are injected into the mouse, the mouse will reject or fight the tumor cells and cancer will not develop or decrease the tumor bourdon. However, if a mouse has not been vaccinated, it will develop cancer.

Immuntherapies for preventing, ameliorating and/or treating cancer and tumorous diseases by means of using whole cell vaccines (WCV) have the advantage of being multivalent with respect to tumor-antigens, however WCVs are often only weakly immunogenic. In general, it is to be distinguished between vaccines comprising vital whole tumor cells (WCV) and vaccines comprising lysed tumor cells (TCLV) (Sivanandham (2000), Biological Therapy of cancer, Ed. Rosenberg, S. A., 632-647).

Whole cell vaccines (WCV) have the advantage that tumor cells can be genetically engineered before being vaccinated and, therefore, used as a vehicle for substances that have an immunostimulatory effect (Mach (2000), Curr. Opin. Immunol. 12, 571-575). However, the disadvantages of this therapy are the high technical expense of genetically engineering said cells, the problems of keeping a high quality standard in the production of whole cell vaccines and the ethical problems accompanying the administration of vital tumor cells as vaccines (Sivanandham (2000), loc. cit.).

With respect to WCV, several publications showed that the kind of cell death influences the immune response (Melcher (1999), J. Mol. Med. 77, 824-833). Additionally, it was found that the expression of heat shock proteins influences the immune response against cells (Galucci (2001), Curr. Opin. Immunol. 13, 114-119; Todryk (2000), Immunology 163, 1398-1408). Moreover, a large number of methods to induce cell-death, in particular, apoptosis, exists which strongly influence the immunogenicity of apoptotic tumor cells (Restifo (2000), Curr. Opin. Immunol. 12, 597-603). With respect to WCV various publications showed that vital necrotic tumor cells are both in vitro and in vivo, i.e. in the animal model system, more immunogenic than apoptotic or untreated cells. In those publications cell death was chemically induced by gancyclovir in tumor cells, which express the herpes simplex virus (HSV) thymidine kinase (HSVtk). Said HSV thymidine kinase functions as a so-called "suicide-gene" if for example induced by gancyclovir. However, cell death only occurs after applying gancyclovir if the cells carrying the recombinant HSV thymidine kinase gene, additionally harbour the anti-apoptotic gene bcl-2. Whereas HSV thymidine kinase positive and bcl-2 negative cells undergo programmed cell death after induction of HSV thymidine kinase by gancyclovir. Only the use of HSVtk and bcl-2 positive whole tumor cells for prophylactic vaccination of mice and the subsequent administration of gancyclovir resulted in a protection of the animals against the development of tumors (Gough (2001), Cancer Res. 61, 7240-7247; Melcher (1998), Nat. Med. 4, 581-587). It was also observed that macrophages phagocytosed both necrotic and apoptotic tumor cells, however, reacted differently with respect to said tumor cells. On one hand immunstimulatory cytokines, like TNFα or IL-1β were secreted if the macrophages phagocytosed necrotic cells, on the other hand immune-suppressive cytokines, like IL-10 were secreted if apoptotic cells were phagocytosed (Gough (2001), loc. cit.). Moreover, macrophages which were co-cultivated either with tumor cells incubated for 1 hour at 45° C. or tumor cells incubated for 15 minutes at 45° C. were tested for their cytokine secretion pattern. If challenged with tumor cells, which were heat-induced for 1 hour, the macrophages reacted similarly like those challenged with chemically induced necrotic cells with respect to the secretion of cytokines. Whereas tumor cells which were heat-induced for 15 minutes resembled apoptotic cells in that they caused secretion of immune-suppressive cytokines after being phagocytosed by macrophages (Gough (2001), loc. cit.).

In contrast to the above-mentioned findings, it was found that living apoptotic tumor cells are as immunogenic as necrotic tumor cells or even more immunogenic (Kotera (2001), Cancer Res. 61, 8105-8109; Restifo (2000), loc. cit.; Shaif-Muthana (2000), Cancer Res. 60, 6441-6447); Albert (1998), Nature 392, 86-89). In these publications other methods than those used in the above-mentioned publication for induction of cell death were performed. For example, Kotera (2001) (loc. cit.) could not find a difference between allegedly necrotic cells, which were generated by freezing and thawing and apoptotic cells, which were generated by UV-B treatment when analysing the activation of dendritic cells. The same was observed in an animal model system when investigating the prophylactic and therapeutic efficacy of dendritic cells, which had taken up either the allegedly necrotic, or apoptotic cells. Shaif-Muthana (2000) (loc. cit.) compared the immunogenicity of radioactive irradiated apoptotic cells with allegedly necrotic cells incubated for 30 minutes at 50° C. It was shown that only apoptotic cells could activate T-cells after dendritic cells had phagocytosed them. Restifo (2000) (loc. cit.) pointed out that it depends on the method for induction of apoptosis to generate immunogenic apoptotic cells. In particular, apoptotic cells caused by viral infection showed up to be highly immunogenic.

In summary, in view of the above discussed it appears as if different parameters of whole cell vaccines influence immunogenicity. In particular, whole cell vaccines may arise from apoptotic or necrotic cells and, thus, may have either stimulatory or suppressive effects on the cells of the immune system. Additionally, the efficacy of whole cell vaccines on components of the immune system, in particular, macrophages, dendritic cells or T-cells also varies. Another variable parameter, which seems to influence the immunogenicity of whole cell vaccines, is the kind of technique to induce cell death.

Tumor cells have also been treated with dinitrophenol or fixed with glutaraldehyde in order to improve the immunogenicity before being used as whole cell vaccines (Berd (1997), J. Clin. Oncol. 15, 2359-2370; Sensi (1997), Clin. Invest. 99, 710-717; Fujiwara (1984), J. Immunol. 133, 509-514; Price (1979), Br. J. Cancer 40, 663-665). Additionally, tumor cells have also been treated by physical means, i.e. applying them to high pressure before administration as whole cell vaccines (U.S. Pat. No. 4,931,275). It is of note that these strategies for improving immunogenicity may be problematic in that the used chemicals have to be removed without leaving any residues.

A different approach for treating cancer is hyperthermia. Thereby, tumor tissue is treated with heat. This heat-treatment by is based on the finding that tumor cells are more sensitive to heat than normal cells (Cavaliere (1967), Cancer 20, 1351-1381; Dickson (1979), Lancet 1, 202-205). The aim of many workers in the field of hyperthermia was to demonstrate that tumor cells could be killed in vivo and in vitro by heat. Thus, vital tumor cells were treated with temperatures ranging from 39° C. to 46° C. to analyse their vitality after the treatment either in cell culture or in an animal model system (Cavaliere (1967), loc. cit.; Giovanella (1970), Cancer Res. 6, 1623-1631; Selawry (1957), Cancer Res. 17, 785-791). Besides the vitality of treated tumor cells, also the immunogenicity of said cells was analysed (Bourdon (1981), Ann. Immunol. 1, 43-63; Mise (1990), Cancer Res. 50, 6199-6202; Check (1974), Cancer 34, 197-203; Mondovi (1972), Cancer, 4 885-888; Price (1979), loc. cit.). Mise (1990) (loc. cit.) has isolated cytotoxic T-cells from mice to which tumor cells have been administered and has analysed the ability of T-cells to lyse tumor cells in vitro. In these experiments it was observed that tumor cells, which had been incubated at 42° C. for 30 minutes, were more efficiently lysed than untreated tumor cells. Other studies could also show the beneficial effect of hyperthermia on the lysis of tumor cells by cells of the immune system.

Clinically hyperthermia is used by applying an increased temperature to the tumor in vivo in order to achieve a killing of the cells in vivo. Therefore, during a hyperthermia treatment a patient is not immunized with tumor cell derived vaccines.

Another approach for prophylactic and therapeutic vaccination against tumors are tumor cell lysate vaccines (TCLV). The advantages of tumor cell lysate vaccines over the aforementioned approaches for vaccination and treatment of cancer are the simple method of production, which is not or much less subjected to fluctuations in keeping a high quality standard since tumor cells are killed or lysed before administration. Said killing or lysing can be done mechanically or by freezing/thawing. Additionally, bacterial or viral adjuvants, e.g. Calmette-Guerin (BCG) (Mitchell (1988), Cancer Res. 48, 5883-93) or vaccinia virus (Berthier-Vergnes (1994), Cancer Res. 54, 2433-2439) have been described to improve immunogenicity of tumor cell lysate vaccines.

TCLV are produced by mechanically or enzymatically gaining tumor cells from tumor tissue originating from primary tumor material, metastases and the like to small pieces and by subsequently lysing and killing them by repeated freezing and thawing—in contrast to whole cell vaccines (WCV). The lysates produced in that manner are so-called "necrotic lysates" (Gallucci (1999), Nat. Med., 11, 1249-55; Kotera (2001), loc. cit.; Restifo (2000), loc. cit.; Sauter (2000), J. Ex. Med., 191, 423-34).

During the process of the "real" necrotic death a series of genes are activated which are only fragmentally known, however, resulting in the secretion of proteins into the medium which show a pro-inflammatory response. However, altered activation of gene expression is highly unlikely to take place during the rapid freeze/thawing as described in the prior art. Therefore, the above-mentioned positive effects assumed to be connected with "real" necrotic cells (Melcher (1999) J. Mol. Med 77, 824-833) and do not apply to the allegedly "necrotic" cell lysates. Thus, the allegedly "necrotic" cell lysates of the prior art do in fact not comprise relevant necrotic cells in the sense of the invention.

Heat shock proteins are amongst the gene products, Which are suggested to be involved in the immunological effects of necrotic cells on the immune system (Gallucci (2001), Curr. Opin. Immunol. 13, 114-119; Todryk (2000), loc. cit.). By now many signals have been identified which cause an increased expression of HSPs. Heat shock proteins (HSPs), belong to the group of stress proteins which are present in all cells in all life forms. They are induced when a cell undergoes various types of environmental stresses like heat, cold and oxygen deprivation.

HSPs are also present in cells under perfectly normal conditions. They act like "chaperones," making sure that the cell's proteins are in the right shape and in the right place at the right time. For example, HSPs help new or distorted proteins fold into shape, which is essential for their function. They also shuttle proteins from one compartment to another inside the cell, and transport old proteins to "garbage disposals" inside the cell.

For decades it has been known that animals, e.g. mice can be "vaccinated" against cancer and after many experiments, it was found that one element responsible for immunological responses in mice were heat shock proteins. In particular Hsp70 expression has been shown to be linked with induction of cell death. Thus, Hsp70 seems to be at least one important factor involved in the immunstimulatory effects of necrotic cells (Dressel (2000), J. Immunol. 164, 2362-2371; Melcher (1998), loc. cit.; Todryk (2000), loc. cit.). Feng (Feng (2001), Blood 11, 3505-3512) has induced the expression of membrane-bound Hsp70 in cells, which caused improvement of the immunogenicity in an animal model system. In a control experiment these cells have been injected as a lysate into mice without provoking an anti-tumor response. Furthermore, the immunstimulatory role of certain isolated HSPs, in particular Hsp70 and gp96, has been demonstrated (U.S. Pat. Nos. 6,168,793; 5,948,646; 5,961,979; Schild (2000), Nat. Immunol. 1, 100-101; Binder (2000), J. Immunol. 165, 6029-6035; Wells (2000), Immunol. Today 21, 129-132). In addition, HSPs purified from cell lysates have also been described as highly immunogenic molecules, which present peptides to the immune system. Therefore, they are used commercially for the development of tumor vaccines.

In conclusion, there are problems or drawbacks associated with whole cell vaccines (WCV) or hyperthermia and with tumor cell lysate vaccines (TCLV) and in order to develop or to obtain potent vaccines it is important to increase the immunogenicity dramatically. The medical need and commercial interest for an according efficient tumor vaccine, which can be produced easily, cost efficiently and in a highly reproducible way is therefore given.

Thus, the technical problem underlying the present invention is to provide means and methods for improved vaccination against cancers, tumorous diseases, infections and/or autoimmune diseases.

The solution to said technical problem is achieved by providing the embodiments characterized in the claims.

Accordingly, the present invention relates to a process for the production of an immunogenic compound comprising the steps of
(a) inducing necrosis by temperature in tumor cells; and
(b) lysing said necrotic tumor cells so as to obtain a lysate.

Surprisingly it was found that induction of necrosis by temperature leads to an increased immunogenicity of tumor cell lysates both in vitro and in vivo. Even more surprising was the finding that tumor cell lysates harbouring a large amount of heat shock proteins are not as immunogenic as tumor cell lysates which were generated with the inventive process harbouring an amount of heat shock proteins comparable to that of tumor cell lysates from untreated, i.e. non-necrotic tumor-cells. This indicates that the expression of heat shock proteins is not correlated with the increased immunogenic effect of the lysates according to the invention.

According to the present invention the term "tumor cells" means cell lines or cells which can be grown under in vitro culture conditions, or tumor cell lines and primary cell cultures, or tumor cells derived from primary or secondary tumor or metastases as listed herein. The cells can be of autologous, allogeneic, syngenic, or xenogenic origin in relation to the person, patient or animal treated and from the same or from different tissues, organs or cell origin in a species (e.g. in case of cancer treatment or prevention in relation to the treated or to be prevented cancer type). The tumor cells used in the process can also be mixtures of the above-mentioned tumor cells. In a preferred embodiment those tumor cells can be altered via mutagenesis, infection with pathogenic particles, like viruses, bacteria, fungi, parasites, or via gentechnological methods, thereby introducing novel antigens or immunogens or parts thereof. In particular, the introduced antigens or immunogens or parts thereof can be of tumors or infectious diseases origin or can be connected with these diseases.

In accordance with the present invention, the term "necrotic tumor cells" means a cell population containing at least 15% necrotic cells as determined for example by the techniques mentioned hereinbelow.

When the tumor cells are derived from tumors or metastases, also including micrometastases, they can, e.g., be obtained by surgery, biopsy, or the like.

The tumor cells can be derived from any possible type of tumors. Examples are skin, breast, brain, cervical carcinomas, testicular carcinomas, head and neck, lung, mediastinum, gastrointestinal tract, genitourinary system, gynaeco-logical system, breast, endocrine system, skin, childhood, unknown primary site or metastatic cancer, a sarcoma of the soft tissue and bone, a mesothelioma, a melanoma, a neoplasm of the central nervous system, a lymphoma, a leukaemia, a paraneoplastic syndrome, a peritoneal carcinomastosis, a immunosuppression-related malignancy and/or metastatic cancer etc. The tumor cells may, e.g., be derived from: head and neck, comprising tumors of the nasal cavity, paranasal sinuses, nasopharynx, oral cavity, oropharynx, larynx, hypopharynx, salivary glands and paragangliomas, a cancer of the lung, comprising non-small cell lung cancer, small cell lung cancer, a cancer of the mediastinum, a cancer of the gastrointestinal tract, comprising cancer of the oesophagus, stomach, pancreas, liver, biliary tree, small intestine, colon, rectum and anal region, a cancer of the genitourinary system, comprising cancer of the kidney, urethra, bladder, prostate, urethra, penis and testis, a gynaecologic cancer, comprising cancer of the cervix, vagina, vulva, uterine body, gestational trophoblastic diseases, ovarian, fallopian tube, peritoneal, a cancer of the breast, a cancer of the endocrine system, comprising a tumor of the thyroid, parathyroid, adrenal cortex, pancreatic endocrine tumors, carcinoid tumor and carcinoid syndrome, multiple endocrine neoplasias, a sarcoma of the soft tissue and bone, a mesothelioma, a cancer of the skin, a melanoma, comprising cutaneous melanomas and intraocular melanomas, a neoplasm of the central nervous system, a cancer of the childhood, comprising retinoblastoma, Wilm's tumor, neurofibromatoses, neuroblastoma, Ewing's sarcoma family of tumors, rhabdomyosarcoma, a lymphoma, comprising non-Hodgkin's lymphomas, cutaneous T-cell lymphomas, primary central nervous system lymphoma, and Hodgkin's disease, a leukaemia, comprising acute leukemias, chronic myelogenous and lymphocytic leukemias, plasma cell neoplasms and myelodysplastic syndromes, a paraneoplastic syndrome, a cancer of unknown primary site, a peritoneal carcinomastosis, a immunosuppression-related malignancy, comprising AIDS-related malignancies, comprising Kaposi's sarcoma, AIDS-associated lymphomas, AIDS-associated primary central nervous system lymphoma, AIDS-associated Hodgkin's disease and AIDS-associated anogenital cancers, and transplantation-related malignancies, a metastatic cancer to the liver, metastatic cancer to the bone, malignant pleural and pericardial effusions and malignant ascites. It is mostly preferred that said cancer or tumorous disease is cancer of the head and neck, lung, mediastinum, gastrointestinal tract, genitourinary system, gynaecological system, breast, endocrine system, skin, childhood, unknown primary site or metastatic cancer, a sarcoma of the soft tissue and bone, a mesothelioma, a melanoma, a neoplasm of the central nervous system, a lymphoma, a leukemia, a paraneoplastic syndrome, a peritoneal carcinomastosis, a immunosuppression-related malignancy and/or metastatic cancer. Accordingly, the term "tumor cell" as provided herein, includes in particular a cell afflicted by any one of the above-identified conditions, but is not limited to the mentioned conditions.

The tumor cells are provided in step (a) of the process according to the invention in a form which allows to induce necrosis by temperature.

The tumor cells may be in any state or form, which allows inducing necrosis. They may, e.g., be in the form of fresh material or can be taken from previously frozen material. In a preferred embodiment the previously frozen material in form of cell lines is thoroughly thawed and cultivated. If tumor material is used, it is preferably material which has already been treated mechanically and/or enzymatically so as to provide smaller tissue pieces and/or separate cells.

The resulting cells or tissue pieces are treated afterwards by temperature in order to induce necrosis or are cultivated for a suitable time in vitro.

In the context of the present invention the term "necrosis" means morphological changes of cells. Necrosis is, inter alia, characterized for example by "leakiness" of the cell membrane, i.e. an increased permeability which also leads to an efflux of the cell's contents and an influx of substances perturbing homeostasis and ion-equilibrium of the cell, DNA fragmentation and, finally, to the generation of granular structures originating from collapsed cells, i.e. cellular debris. Typically, necrosis results in the secretion of proteins into the surrounding which, when occurring in vivo, leads to a pro-inflammatory response.

Methods for the determination whether a cell is necrotic or not are known in the prior art and are also described in the examples herein. It is not important which method the person skilled in the art chooses since various methods are known.

However, it is important to distinguish between an apoptotic cell undergoing the so-called programmed cell death and a necrotic cell. Necrotic cells in accordance with the present invention can be determined, e.g., by light-, fluorescence or electron microscopy techniques, using, e.g., the classical staining with trypan blue, whereby the necrotic cells take up the dye and, thus, are stained blue, or distinguish necrotic cells via morphological changes including loss of membrane integrity, disintegration of organelles and/or flocculation of chromatin. Other methods include flow cytometry, e.g., by staining necrotic cells with propidium iodide. The preferred propidium iodide staining is described in detail in the examples herein. Apoptotic cells can be determined, e.g., via flow-cytometric methods, e.g., attaining with Annexin V-FITC, with the fluourchrome: Flura-red, Quin-2, with 7-amino-actinomycin D (7-AAD), decrease of the accumulation of Rhodamine 123, detection of DNA-fragmentation by endonucleases: TUNEL-method (terminal deoxynucleotidyl transferase caused X-UTP nick labelling), via light microscopy by staining with Hoechst 33258 dye, via Western blot analysis, e.g., by detecting caspase 3 activity by labelling the 89 kDa product with a specific antibody or by detecting the efflux of cytochrome C by labelling with a specific antibody, or via agarose gel DNA-analysis detecting the characteristic DNA-fragmentation by a specific DNA-ladder.

The preferred technologies are described in detail in the examples herein, and are the propidium iodide staining for necrotic cells and the annexin staining for apoptotic cells, whereby apoptotic cells are only stained by annexin V and necrotic cells are stained by propidium iodide and annexin V (Vermes (1995), J. Immun. Meth. 184, 39-51). This flow-cytometry allows rapid and easy qualitative and quantitative measurements.

Preferably, necrosis is determined by flow cytometry, even more preferred is flow cytometry using Annexin V/propidium iodid staining and most preferred is the method as described in the examples herein.

The term "inducing necrosis by temperature" in the context of the present invention means that in a percentage of at least 15%; preferably in more than 40% and herein preferred at least in 70% of the cells of the cell population of the tumor cells changes which result in necrosis.

Methods for measuring said temperature, which is used for inducing necrosis, are known to the person skilled in the art. Preferably, said temperature can be measured by physical means. Said physical means is preferably an optical, mechanical or electrical thermometer, whereby it is understood that normal physical fluctuation in the measurement of a temperature due to errors in the measurement or physical inertia of the means are in the acceptable range of measurement tolerances. Most preferably, said physical means for measuring temperatures are incorporated by the supplier in the means or in the apparatus used for heat-induction. However, it is also preferred that the temperature may be measured directly within the sample of tumor cells undergoing temperature-induction.

The temperature for inducing necrosis in the cells can be applied to the cells by means and methods known to the person skilled in the art. Possible methods are, e.g., the incubation in heated air or water or irradiation. Suitable means are, e.g., heating blocks, thermal heaters, water bathes incubators, heating rods and the like.

It was surprisingly found that cell lysates produced from tumor cells in which necrosis was induced by temperature as described herein are superior to those of the prior art since their immunogenicity is increased significantly.

It is important to note that the necrotic cell lysates consist of cell populations with the mentioned percentages of relevant necrotic cells as defined above, while cell lysates, which are sometimes called necrotic cell lysates in the literature and which correspond to cells lysed directly without induction of necrosis via rapid freeze/thawing, are called non-treated cells or non-treated cell lysates in the examples herein.

In accordance with the present invention the term "lysing" relates to various methods known in the art for opening/destroying cells. The method for lysing a cell is not important and any method that can achieve lysis of the tumor cells may be employed. An appropriate one can be chosen by the person skilled in the art, e.g. opening/destruction of cells can be done enzymatically, chemically or physically. Non-limiting examples for enzymes and enzyme cocktails are proteases, like proteinase K, lipases or glycosidases; non-limiting examples for chemicals are ionophores, like nigromycin, detergents, like sodium dodecyl sulfate, acids or bases; and non-limiting examples of physical means are high pressure, like French-pressing, osmolarity, temperature, like heat or cold. Additionally, a method employing an appropriate combination of an enzyme other than the proteolytic enzyme, an acid, a base and the like may also be utilized.

According to the present invention the term "lysate" means a solution or suspension in an aqueous medium of cells that are broken. However, the term should not be construed in any limiting way. The cell lysate comprises, e.g., macromolecules, like DNA, RNA, proteins, peptides, carbohydrates, lipids and the like and/or micromolecules, like amino acids, sugars, lipid acids and the like, or fractions of it. Additionally, said lysate comprises cell debris which may be of smooth or granular structure. The details of the preparations are specifically described in the examples of the present specification. Accordingly, those skilled in the art can prepare the desired lysates by referring to the above general explanations and specific explanations in the examples, and appropriately modifying or altering those methods, if necessary. Preferably, said aqueous medium is water, physiological saline, or a buffer solution that any solid mass cannot be observed without help of optical means, and that the dispersoids can be phagocytosed by the antigen-presenting cells. An advantage of the tumor cell lysate obtainable by the processes of the present invention is that it can be easily produced as described in the appended Examples and stored cost efficiently since less technical facilities are needed.

However, said lysate is not limited to necrotic cells since, for example, due to the different sensitivity of the treated cells or due to the applied conditions for the temperature-induction of cells also apoptotic cells can be part of the cell population from which the lysate is obtained. Nevertheless, necrotic cells have to be at least 15% of the cell population, preferably more than 40%, particularly more than 70%. The determination of the percentages may vary from experiment to experiment due to measuring inaccuracies occurring in the technology of flow cytometry and the possibility of varying interpretations of the data and setting of the gates. Accordingly, a deviation of 10%, preferably of 5% and more, preferably of 1% may occur if a method other than that specifically described in the examples is used.

Preferably, the tumor cells are lysed by freezing and thawing, more preferably freezing at temperatures below −70° C. and thawing at temperatures of more than 30° C., particularly freezing is preferred at temperatures below −75° C. and thawing is preferred at temperatures of more than 35° C. and most preferred are temperatures for freezing below −80° C. and temperatures for thawing of more than 37° C. It is also preferred that said freezing/thawing is repeated for at least 1 time, more preferably for at least 2 times, even more preferred for at least 3 times, particularly preferred for at least 4 times and most preferred for at least 5 times.

According to the invention, lysates are also preparations of fractions of molecules from the above-mentioned lysates. These fractions can be obtained by methods known to those skilled in the art, e.g., chromatography, including, e.g., affinity chromatography, ion-exchange chromatography, size-exclusion chromatography, reversed phase-chromatography, and chromatography with other chromatographic material in column or batch methods, other fractionation methods, e.g., filtration methods, e.g., ultrafiltration, dialysis, dialysis and concentration with size-exclusion in centrifugation, centrifugation in density-gradients or step matrices, precipitation, e.g., affinity precipitations, salting-in or salting-out (ammoniumsulfate-precipitation), alcoholic precipitations or other proteinchemical, molecular biological, biochemical, immunological, chemical or physical methods to separate above components of the lysates. In a preferred embodiment those fractions which are more immunogenic than others are preferred. Those skilled in the art are able to choose a suitable method and determine its immunogenic potential by referring to the above general explanations and specific explanations in the examples herein, and appropriately modifying or altering those methods, if necessary.

The induction of necrosis by temperature according to step (a) of the method according to the invention is preferably achieved by incubation of the tumor cells at a temperature which is above the average body temperature of the organism from which the cells are derived, preferably at a temperature above 37° C. More preferably, the cells are incubated at a temperature of more than 38° C., even more preferably of more than 39° C., particularly preferred of more than 40° C. and most preferred of more than 41.5° C.

It is preferred that the temperature is chosen in a way that although necrosis is induced, no or only a low increase in hsp70 expression is induced. By a "low increase" an increase of preferably not more than a factor of 2 is meant. The corresponding temperature can depend on the specific cell type used but can be easily determined by the skilled person by routine experimentation, e.g. by incubating the corresponding cells at different temperatures and determining the amount of necrotic cells and the level of hsp70 expression at different temperatures using methods as those shown in the examples herein.

In an even more preferred embodiment the tumor cells are incubated at a temperature of more than 41.2° C., more preferably at a temperature of more than 42° C., more preferably at a temperature in the range of 45° C. to 55° C., even more preferred in the range of 45.5° C. to 47° C. In a most preferred embodiment the cells are incubated at a temperature in the range of 46.0° C. to 46.4° C., in particular at about 46.2° C.

As shown in the examples herein, temperatures of about 46.2° C. used for inducing necrosis lead to a surprisingly high amount of necrotic cells and an unexpectedly high increase in immunogenicity.

Moreover, it is demonstrated in the examples herein that tumor cell lysates produced from tumor cells in which necrosis has been induced by temperature of about 46.2° C. have also surprising effects in vivo. Comparable results were also achieved with cell lysates from the same cell line induced at 46° C.

In particular, mice immunized with the tumor cell lysates of the present invention showed immune reactions against the antigens present on the tumor cells used for the production of the cell lysates. Said mice developed antibodies of the IgG-type that can only be produced if a so-called class-switch has occurred. Said class-switch is only possible if T helper cells are included in the immune response to antigens. Moreover, it was also surprisingly found that the immunized mice developed said IgG-type antibodies against carbohydrate antigens for which so far only IgM-type antibodies have been developed by mice. However, IgM-type antibodies can be produced without a class-switch that implies that T helper cells had not been involved. Thus, the tumor cell lysates of the present invention are advantageous as regards immunogenicity and are favourable for vaccination against cancer, tumorous diseases, infections and/or autoimmune diseases since they evoke an immune response in which also B- and T-cells are involved.

The incubation of the tumor cells at a specific temperature is carried out for a period of time sufficient to induce necrosis and depends on the temperature and the means and methods for producing it. It is of note that the person skilled in the art knows that the time needed for induction of necrosis in said tumor cells may vary depending, inter alia, on the cells used, the status of the cells, the conditions in the culture medium, the sensitivity of the cells and the like. Moreover, the time for induction of necrosis may also depend on the kind of applying the temperature to the cells and on the apparatus used for applying the temperature. Moreover, the time for inducing said necrosis is also dependent on the temperature at which the cells have been incubated for the induction of necrosis. The most preferable temperature may also vary depending on the type and source of the tumor cells.

Generally, the incubation should last for a period of time of at least 1 minute. Preferably, the induction lasts for a period of time of at least n minutes, wherein n is an integer in the range of 2 to 60, with n=15 being particularly preferred. More preferably, the incubation lasts at least 1 hour, even more preferred at least 2 hours and particularly preferred at least 3 hours. More preferably between 1.5 and 5 hours. The most preferred incubation is between 2 and 3 hours.

There is in principle no upper limit for the time of incubation. However, it is preferably no longer than 48, 36, 24, 12, 11, 10, 9, 8, 7, 6, 5 or 4 hours.

In an advantageous preferred embodiment the necrotic cells are directly lysed after the temperature induction of necrosis after temperature-induction of necrosis.

In a preferred embodiment the necrotic cells obtained after step (a) of the process according to the invention are further incubated before lysing them. As shown in the examples herein, this further incubation also influences the amount and immunogenicity of necrotic cells. Said further incubation is preferred to be performed at a temperature of more than 35° C., even more preferably at a temperature of more than 36° C., particularly preferred at a temperature of about 37° C. The time for this further incubation is preferred to be at least 0.1 hour, more preferably to be at least 2 hours, even more preferred to be at least 3 hours, particularly preferred to be at least 6 hours, even more particularly preferred to be at least 12 hours and most preferred to be at least 22 hours.

In a preferred embodiment of the invention, it is envisaged that in the process of the present invention more than 15% of said induced tumor cells are necrotic.

As mentioned herein above, due to, e.g., the different sensitivity of the treated cells, due to the applied conditions for the temperature-induction of cells or due to different conditions in culturing the tumor cells that consist of a population of the cells also comprising apoptotic cells which are subsequently lysed together with the other cells of the population also comprising the necrotic cells according to the described process.

In order to obtain an effective immunogenicity it is desirable to obtain a certain percentage of necrotic cells in the lysate. Accordingly, the process is preferably designed so as to result in more than 15, 20, 21, 22, 23, 24, 25, 30, 35, 40, 45, 50, 55, 60, 65, 70, 75, 80, 82, 84, 86, 87, 88, 89, 90, 92, 94, 96, 98, 99% of the temperature-induced tumor cells being necrotic. Most preferably, more than 40% or 70% of said tumor cells are necrotic. It is of note that the amount of necrotic cells can also depend on the temperature, time and time for regeneration after induction of necrosis by temperature as demonstrated in the examples herein as well as on the type and source of the tumor cells.

Also preferred is that the tumor cells used in the process according to the invention are genetically engineered, mutated or infected by oncogenic viruses.

In the context of the present invention the term "genetically engineered" is used in its broadest sense for methods known to the person skilled in the art to modify desired nucleic acids in vitro and in vivo such that genetic modifications are affected and genes are altered by recombinant DNA technology. Accordingly, it is preferred that said methods comprise cloning, sequencing and transformation of recombinant nucleic acids. For this purpose appropriate vectors, primers, enzymes, host cells and the like can be used and are known by the skilled artisan. Preferably, genetically engineered tumor cells comprise cells harbouring recombinant nucleic acids encoding antigens or immunogens or parts thereof, cytokines, chemokines, growth factors and the like. Antigens and immunogens can be, for example, one or more tumor antigens or parts thereof, antigens from infectious microorganisms or parasites, like bacteria, fungi, viruses and the like. Furthermore, among the immunogens are, for example, molecules which increase the immunogenicity, like pan T-cell epitopes or multimers thereof, like PADRE-epitopes, or tetanus toxoid fragments which evoke an additional immunstimulatory effect via activation of MHC class II-mediated processes.

Also preferred are tumor cells genetically engineered with nucleic acids encoding effector molecules, like transcription factors, components of signal transduction pathways or signalling cascades, or cytokines, chemokines, growth factors and the like which are able to modulate directly or indirectly the expression of endogenous molecules, e.g. nucleic acids, polypeptides, posttranslationally modified polypeptides and lipids and the like. More preferably, the tumor cells are transiently or stably transfected with a desired nucleic acid molecule.

It is also preferred that the tumor cells are genetically engineered so as to express a polypeptide against which antibodies should be raised. If cell lysates from these tumor cells are produced and administered to an individual, it is expected that a humoral and/or cellular immune response is developed by individuals, preferably this immune response comprises antibody responses and/or T helper cell responses and/or cytotoxic T cell responses.

In accordance with the present invention, the term "mutated" means (a) permanent modification(s) of genetic material, i.e. nucleic acids, caused, for example, naturally or by physical means or chemical compounds/substances/agents. Said modifications include point mutations, like transitions or transversions, deletion/insertion/addition of one or more bases within a nucleic acid/gene/chromosome thereby modifying the nucleic acid/gene/chromosome which can cause, inter alia, aberrant gene expression/transcription/translation or inactive gene products, constitutive active/inactive gene products leading to e.g. dominant-negative effects. Thus, it is also preferred that the tumor cells comprise cells which harbour (a) mutation(s) in (a) desired gene(s) or in which (a) mutation(s) in (a) desired gene(s) is induced by methods known to the person skilled in the art. It is also known in the prior art that mutated or genetically engineered tumor cells can be selected by any suitable method/phenotype.

In accordance with the present invention the term "infected" means cells, which have been infected with a virus, or viroid, and/or proteinaceous structure. Said virus, or viroid, and/or proteinaceous structure may also be used as a vehicle for genetically engineering said cells. It is preferred that said virus which infects tumor cells is an oncogenic virus, however, is not limited to oncogenic viruses. Most preferably said oncogenic virus is selected from the group consisting of retroviruses or DNA viruses, e.g. papovaviruses like human papilloma viruses (HPV), type C oncoviruses, like human T cell leukaemia viruses (HTLV), herpes viruses, like Epstein-Barr virus (EBV), hepadnaviruses, like hepatitis B virus (HBV), and lentiviruses, like human deficiency virus (HIV). It is also preferred that tumor cells are already infected with any one of the above mentioned viruses. Furthermore, infected tumor cells or lysates thereof may be important when used for prophylactic/therapeutic vaccination against infectious diseases caused for example by viruses like HIV, HBV, hepatitis C virus (HCV), HPV. Preferably, the infectious component(s) comprised by the lysates produced from these infected cells has/have to be additionally inactivated. Methods to be used are known to those skilled in the art, e.g., heat inactivation, acid inactivation and/or sterile filtration or the like.

Moreover, in another preferred embodiment of the present invention the tumor cells are autologous.

In the context of the present invention the term "autologous" means that the tumor cells are derived from the same individual to which the lysate resulting from the process according to the invention shall be later administered. One advantage is by using cells from the autologous tumor that there are a large variety of relevant and suitable antigens in the lysate for treating cancers or tumorous diseases of the individual or prevent its recurrence or relapse.

Alternatively, in another preferred embodiment the tumor cells are allogeneic. In the context of the present invention the term "allogeneic" means that the tumor cells are derived from an individual which is different from the individual to which the lysate resulting from the process according to the present invention shall be later administered. A herein further preferred embodiment of the allogeneic tumor cells for use in an allogeneic setting are tumor cells of a patient, or cells originating from these cells, which were successfully used for immunization of that latter patient in a autologous setting resulting in a partial or complete reduction of tumor load.

In the context of the present invention the term "allogeneic tumor cells" further comprises cell lines, including cell lines, e.g., tumor cell lines, or cell lines or cultures from primary material and the like, which are not originating from the individual to which the lysate shall be administered. The advantage of allogeneic tumor cells are antigens or immunogens which are not shared by the cancers or tumorous diseases to be treated or prevented, resulting in an immune response comprising a strong danger signal and/or helper response which can be favourable to overcome anergies or tolerances.

Alternatively, in a preferred embodiment the tumor cells are xenogenic. In the context of the present invention the term "xenogenic" means that the tumor cells comprise tumor cells from primary or secondary tumors or from metastases, cell lines, e.g., tumor cell lines, immortalized cell lines or cell lines or cultures from primary material and the like, which are not originating from the same species to which the lysate shall be later administered.

Alternatively, in another preferred embodiment the tumor cells are allogeneic, autologous or xenogenic and are of a different tissue or cell source or the like than the cancers or tumors, e.g. tumor cells from a mammary tumor cell line are used for generating a lysate according to the process of the invention which is administered to an individual for prophylaxis or treatment of colon or gastric cancers or tumorous diseases, or a lysate according to the invention from a mutated myeloma cell line for use in an individual for prophylaxis or treatment of carcinomas. Preferably, these cell lines have one or more antigens which are shared with the cancers or tumorous diseases to be treated. The advantage is an additional strong response against antigens or immunogens foreign to the cancers or tumorous diseases to be treated or prevented, e.g., antigens specific for the tumor cell which are not shared by the cancer or tumors to be treated or prevented, comprising a strong danger signal and/or helper response which can be favourable to overcome anergies and/or tolerances. In a preferred embodiment the tumor cells are in addition from an allogeneic source which can in addition have a strong allo-response which can be further favourable to overcome anergies and/or tolerances.

In a preferred embodiment, the lysate is prepared from tumor cells of different types or different lysates prepared from different types of tumor cells are used in combination for the administration to an individual.

More preferably the tumor cells of the lysate or the combination of lysates are allogeneic and autologous tumor cells. Even more preferably, they are a mixture from tumor cells from the same tissue or cell source and the like together with those from a different tissue or cell source and the like. It is, e.g., possible to use a cell lysate from an allogeneic mutated myeloma cell line with a lysate from colon cancer cells from the individual to which the lysate(s) shall be later administered. The advantage is the combination of large amounts of shared antigens from autologous material with the allogeneic part and, therefore, an increased helper, response, allo-response and/or danger signals in order to break potential tolerances and/or anergies of the cancers or tumors. Another example is the mixture of the above allogeneic myeloma cell line with another colon or gastric cancer cell line for the administration to an individual to treat or prevent colon carcinoma. The advantage of the latter is the possibility to generate a potent "off-the-shelf" vaccine with a mixture of large amounts of tumor antigens and an increased helper response, allo-response and/or danger signals in order to break potential tolerances and/or anergies.

The tumor cells can be mixed before the induction of necrosis by temperature induction or after induction but before the lysis or after the lysis. The skilled artisan is able to determine which is favourable for the use for the production, regulatory issues, application to an individual and for its cancers or tumorous diseases.

The examples of the present invention demonstrate that both, an autologous and allogeneic system, can be used for increasing the imunogenicity. As described hereinabove, the process of the present invention allows to produce highly efficient immunogenic compounds by inducing necrosis in the tumor cells and subsequently lysing the cells. The obtained tumor cell lysates can be used for the therapeutic or prophylactic treatment of cancer, tumorous diseases, infections and/or autoimmune diseases.

In this contex the term "immunogenic compound" means compounds having the ability to evoke immune reactions of the cells of the immune system like macrophages, dendritic cells, Langerhans' cells; B- (B1 and B2) and/or T-cells (cytotoxic T cells (Tc), T-helper cells (Th0, Th1 and Th2)), natural killer cells (NK cells), memory cells and the like Preferably, the term "immunogenic compound" means compounds having the ability to evoke humoral and/or cellular immune response, wherein at least one of the cells/group of cells of immune effector cells or cell products of said immune effector cells, for example one or more of the aforementioned cells are involved. The person skilled in the art is aware of various methods to determine whether an immune response is evoked. Examples for methods used for this purpose are shown in the examples and be transferred, where necessary by those skilled in the art, to determine the response in an individual or patient treated with the lysates according to the invention. Furthermore, other methods known to those skilled in the art can complement these techniques. In general, an immunogenic compound leads to an immune response comprising humoral and/or cellular responses, normally comprising that genes or gene products that affect the level of immune responses are expressed/activated, e.g. those of the major histocompatibility class (MHC) I and II, those of antibody light and heavy chains, those of members of the immunglobulin superfamily, those of T-cell receptor/receptor compounds, those of cytokines or those of signal transduction cascades involved in transmitting immune responses.

In a preferred embodiment, the tumor cells used for the production of a cell lysate as described herein are NM-F9 (DSMZ deposit No. DSM ACC2606 or NM-D4 cells (DSMZ deposit No. DSM ACC2605)

The term "NM-F9" (also referred herein as "F9" or "TF-positive F9 cells") or "NM-D4" means cell lines or cells derived from the human myelogenous leukemia cell line K562. (ATCC: CCL-243). NM-F9 and NM-D4 were deposited with the Deutsche Sammlung für Mikroorganismen und Zellkulturen GmbH ("DSMZ") on Aug. 14, 2003. The DSMZ is located at the Mascheroder Weg 1b, D-38124 Braunschweig, Germany. The DSMZ deposit was made pursuant to the terms of the Budapest treaty on the international recognition of the deposit of microorganisms for purposes of patent procedure. The NM-D4 cell line has accession number DSM ACC2605. The NM-F9 cell line has accession number DSM ACC2606.

The present invention also relates to a lysate obtainable or obtained by the process according to the present invention and to dendritic cells loaded with such a lysate.

Moreover, the present invention also relates to a composition comprising a lysate or dendritic cells according to the present invention.

In a preferred embodiment said composition is a pharmaceutical composition. In accordance with the present invention the term "pharmaceutical composition" relates to compositions comprising the cell lysates described hereinabove which are obtained by the aforementioned processes and having the desired pharmacological activity. Such pharmaceutical compositions comprise a therapeutically effective amount of the cell lysates of the present invention, and a pharmaceutically acceptable carrier. The pharmaceutical composition may be administered with a physiologically acceptable carrier to a patient, as described herein. In a specific embodiment, the term "pharmaceutically acceptable" means approved by a regulatory agency or other generally recognized pharmacopoeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil; sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the cell lysate, preferably in purified form, together with a suitable amount of carrier so as to provide the form for proper administration to the patient. The formulation should suit the mode of administration.

In another preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilised powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration. The cell lysate of the invention can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

The amount of the cell lysate of the invention which will be effective in the treatment or prevention (in particular by vaccination) of cancers, tumors, tumorous diseases, infections and/or autoimmune diseases can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. Effective doses may be extrapolated from dose-response curves derived from in vitro or animal model test systems.

In another preferred embodiment the composition is a vaccine composition.

In accordance with the present invention the term "vaccine composition" relates to any composition which can be used as a vaccine.

The forms or methods for manufacturing vaccine compositions according to the present invention are not particularly limited, and a composition in a desired form can be prepared by applying a single method available in the field of the art or methods in an appropriate combination. For the manufacture of a vaccine composition, aqueous media such as distilled water for injection and physiological saline, as well as one or more kinds of pharmaceutical additives available in the field of the art can be used. For example, buffering agents, pH adjusting agents, solubilizing aids, stabilizing agents, soothing agents, antiseptics and the like can be used, and specific ingredients thereof are well known to those skilled in the art. The vaccine composition can also be prepared as a solid preparation such as a lyophilized preparation, and then prepared as an injection by adding a solubilizing agent such as distilled water for injection before use. Depending upon the manner of introduction, the compounds may be formulated in a variety of ways as discussed below. The concentration of therapeutically active compound in the formulation may vary from about 0.1-100 wt %. The vaccine composition may be administered alone or in combination with other treatments, i.e., radiation, or other chemotherapeutic agents or anti-cancer agents.

In a preferred embodiment, the vaccine compositions are in a water-soluble form, such as pharmaceutically acceptable salts, which is meant to include both acid and base addition salts.

The vaccine compositions can be prepared in various forms, such as injection solutions, tablets, pills, suppositories, capsules, suspensions, and the like. Pharmaceutical grade organic or inorganic carriers and/or diluents suitable for oral and topical use can be used to make up compositions containing the therapeutically active compounds. Diluents known to the art include aqueous media, vegetable and animal oils and fats. Stabilizing agents, wetting and emulsifying agents, salts for varying the osmotic pressure or buffers for securing an adequate pH value, and skin penetration enhancers can be used as auxiliary agents. The vaccine compositions may also include one or more of the following: carrier proteins such as serum albumin; buffers; fillers such as microcrystalline cellulose, lactose, corn and other starches; binding agents; sweeteners and other flavouring agents; colouring agents; and polyethylene glycol. Additives are well known in the art, and are used in a variety of formulations.

A vaccine composition according to the present invention can be used for immunization against cancer, tumorous diseases, autoimmune diseases and/or infectious diseases.

In another preferred embodiment the composition according to the present invention, in particular the vaccine composition, is optionally combined with an adjuvant or dendritic cells.

In accordance with the present invention "dendritic cells" relate to professional antigen-presenting cells which capture antigens and migrate to the lymph nodes and spleen, where they are particularly active in presenting the processed antigen to T cells. The term "dendritic cells" also means cells which have an activity and function similar to dendritic cells. Dendritic cells can be derived from either the lymphoid or mononuclear phagocyte lineages. Said dendritic cells can be found in lymphatic and non-lymphatic tissue. The latter appear to induce a T cell response only when being activated and having migrated to lymphatic tissues.

Dendritic cells are known to be the or amongst the most potent activators and regulators of immune responses. One important feature is that they are presently the only antigen presenting cells known to stimulate naive T cells. Immature dendritic cells are characterized by their ability to take-up and process antigens, a function that is dramatically reduced in mature dendritic cells, which in turn exhibit enhanced presentation of processed antigens on their surface, mainly bound to MHC Class I and Class II molecules. Maturation is also associated with upregulation of costimulatory molecules (such as CD40, CD80 and CD86), as well as certain other cell surface proteins (e.g. CD83 and DC-Sign). Dendritic cell maturation is also usually associated with enhanced migratory capacity, resulting (in vivo) in migration of dendritic cells to the regional lymph nodes, where the dendritic cells encounter T and B lymphocytes. Dendritic cells can be obtained from individuals using methods known to those skilled in the art and are described in more detail in the examples herein. Furthermore, according to the invention, dendritic cells are also those cells or cell lines which show the comparable functional and/or phenotypic features as dendritic cells, e.g. MUTZ-3 derived cells.

Dendritic cells or their precursors are differentiated using suitable growth factors and/or cytokines, e.g. GM-CSF and IL-4 as shown in the examples herein, the resulting immature dendritic cells are loaded with a lysate according to the invention. Immature DC (iDC) loaded with a lysate according to the invention are further maturated to mature DC (mDC). In special cases also mDC can be loaded (pulsed) with antigens or immunogens from the lysate. Vaccine compositions or pharmaceutical compositions for preventing or treating cancers, tumorous diseases and or infectious diseases preferentially comprise loaded mDC which originate from loaded and matured iDC or which were loaded after or during maturation. Vaccine compositions for autoimmune diseases preferentially comprise loaded iDC which are preferably transiently or stably arrested in the iDC state using methods known to those skilled in the art.

In a preferred embodiment of the invention treatment or prevention of the cancers, tumorous diseases, infections and/or autoimmune diseases and in particular for cancers, tumorous and infectious diseases combines dosages comprising a lysate according to the invention loaded onto dendritic cells with dosages comprising only a lysate according to the invention. The advantage is to combine the ex vivo loading of autologous or allogeneic dendritic cells with the in vivo "loading" of dendritic cells which occurs via the administration of the lysate to an individual. Thereby, different application routes might be preferable. The administration of dendritic cells directly to lymphnodes or other areas with direct contact to the important immune cells to be stimulated by dendritic cells are preferred. The administration of the lysate intradermally, subcutaneously or intrarectally to Payers patches or other areas where dendritic cells or their precursors are located and preferably concentrated, is preferred.

Another preferred embodiment of the invention are vaccine compositions or pharmaceutical compositions comprising a lysate according to the invention loaded onto suitable dendritic cells and adjuvants or costimulatory factors for the enhancement of the action of the dendritic cells, e.g. GM-CSF, interleukins.

With respect to the present invention the term "adjuvant" means that the natural ability of an antigen to induce an immune response can be modified, and in particular enhanced, by altering or by mixing it or loaded dendritic cells described hereinabove with another substance. The term "adjuvant" also means that tumor cells from which the lysates are generated and/or dendritic cells are genetically modified in order to express adjuvants or other factors which influence the immune response, as for example costimulatory factors. The procedure or the substance used to enhance immune responses is called an adjuvant. At least three classes of adjuvants have been used for a long time; these are mineral oil emulsions, aluminium compounds, and surface active materials such as saponin, lysolecithin, retinal, Quil A.RTM., some liposomes, and pluronic polymer formulations. See, for example, Fundamental Immunology, edited by William E. Paul, at p. 1008, Raven Press, New York (this book will hereinafter be referred to as "Fundamental Immunology"). Aluminium adjuvants used alone or in combination include aluminium hydroxide gel, aluminium phosphate, aluminium sulphate, and alums comprising ammonium alum (such as $(NH_4)_2 SO_4.Al_2 (SO_4)_3$) and potassium alum. Aluminium hydroxide (hereinafter "AL") is one of the older adjuvants and it is considered so safe that it has been applied in bacterial and viral vaccines administered to billions of people around the world. Calcium phosphate gel (hereinafter "CP") has similar properties and is also used in vaccines. Both substances are available in pharmaceutical qualities in most countries worldwide. Techniques for preparing adjuvant-antigen preparations for injection are well known in the art. See, for example, Terry M. Phillips, Analytical Techniques in Immunochemistry, pp. 307-10, Marcel Dekker, New York, 1992. Other adjuvants include complete Freund's adjuvant (a water-in-oil emulsion in which killed, dried, mycobacteria—usually *M tuberculosis*—are suspended in the oil phase); incomplete Freund's adjuvant (analogous to the complete Freund's adjuvant with no mycobacteria); ISCOM (or immune stimulating complex, comprising lipophilic particles formed by the spontaneous association of cholesterol, phospholipid and the saponin Quil A.RTM.); lipopolysaccharide (complex molecules consisting of a lipid core—lipid A—with a polysaccharide side chain that are components of certain bacilli, Lipid A is incorporated into the outer membrane of the bacterium and the polysaccharide projects extracellularly. Their adjuvant potency is associated with lipid A; they are also mitogenic for murine B lymphocytes); and mycobacterial adjuvants (whole, heat killed, dried, mycobacteria—such as *M. tuberculosis, M. avium, M. phlei,* and *M. smegmatis*) that, when suspended in mineral oil and emulsifier, have adjuvant activity with respect to any antigen given with them. Extracts of some mycobacteria, e.g., mycobacterial peptidoglycolipids have similar adjuvant activities. See, for example, Dictionary of Immunology at pp. 3, 7, 46, 94, 97, 105, and 116; R. B. Luftig, Microbiology and Immunology, pp. 228-29, Lippincott-Raven Publishers, Philadelphia 1998. Microbial adjuvants include *Corynebacterium parvum* and *Bordetella pertussis*. See, for example, Handbook of Immunology at 115-16. Use of controlled-release preparations and materials with adjuvant activity and possible sites of action have been described in Fundamental Immunology at pp. 1007-09. Mineral carriers such as aluminium hydroxide, potassium ammonium sulphate, and potassium aluminium sulphate adsorb the antigen on their surface. These common adjuvants have been used at a 0.1% concentration with up to 1 mg protein antigen in 1 ml administered to animals at doses of 0.2-0.5 ml/(kg body weight). See Miroslav Ferencik, Handbook of Immunochemistry, p. 115, Chapman & Hall 1993 (this book will hereinafter be referred to as "Handbook of Immunochemistry"). Although Freund's adjuvant is toxic and not used for immunization of human beings, mineral adjuvants such as aluminium hydroxide are common in human medicine. Id. at 116. In addition to alum, other adjuvants in the group of inert carriers include bentonite, latex, and acrylic particles. See Fundamental Immunology at 1008. Combinations of adjuvants can also have adjuvant properties. For example, it has been shown that the combination of saponin and muramyl dipeptide in a squalene in water emulsion is superior to alum as an adjuvant for inducing certain responses in mice. R. Bomford, M. Stapleton, S. Wilson, A. McKnight, and T. Andronova, The control of the antibody isotype responses to recombinant human immunodeficiency virus gp120 antigen by adjuvants, AIDS Res. Hum. Retroviruses Vol. 8(1992) pp. 1765 et seq. These adjuvants are complemented by new adjuvants that have been developed during the last fifteen years. See, for example, Anthony C. Allison, The Role of cytokines in the Action of Immunological Adjuvants, in Vaccine Design. The Role of cytokine Networks, edited by Gregory Gregoriadis and Brenda McCormack, NATO ASI Series A: Life Sciences Vol 293, pp. 1-9, Plenum Press, New York 1997 (this book will hereinafter be referred to as "Vaccine Design"); Immunology at p. 116; H. Snippe, I. M. Fernandez and C. A. Kraaijeveld, Adjuvant Directed Immune Specificity at the Epitope Level. Implications for Vaccine Development. A Model Study Using Semliki Forest Virus Infection of Mice, in Vaccine Design at pp. 155-73. An adjuvant can be administered prior to, simultaneously with, or following the administration of the antigen. Antibody production enhancement caused by adjuvants is not fully understood. However, adjuvant properties that may exist either alone or in various combinations and which permit a substance or formulation to be described as adjuvant active have been defined. See, for example, J. C. Cox and A. R. Coulter, Adjuvants—A classification and review of their modes of action, Vaccine Vol. 15(1981) pp. 248 et seq.; John Cox, Alan Coulter, Rod Macfarlan, Lorraine Beezum, John Bates, Tuen-Yee Wong and Debbie Drane, Development of an Influenza-ISCOM™ Vaccine, in Vaccine Design at pp. 33-49. One of these properties is depot generation, whereby the vaccine is retained near the dose site to give short-term trickle release or a longer term pulsed release. Id. at p. 34.

Preferably, the pharmaceutical or vaccine composition is administered directly or in combination with an adjuvant mentioned herein above or loaded on antigen-presenting cells, particularly dendritic cells. It is also preferred that both the pharmaceutical or vaccine composition and the adjuvant and the pharmaceutical or vaccine composition and the loaded dendritic cells are administered together or separately from each other e.g. at different time points or at different locations.

Additionally, it is also preferred that said pharmaceutical composition and adjuvant is administered together with said pharmaceutical composition loaded on dendritic cells. Since dendritic cells are highly specialized antigen-presenting cells with the unique capability in initiating and regulating antigen-specific immune responses, it is preferred to combine them with the pharmaceutical or vaccine compositions of the present invention. For the preparation of a tumor vaccine dendritic cells can be generated from the peripheral blood of tumor patients from other donors or from the above-mentioned cell lines. In clinical studies, the efficacy of vaccination with dendritic cells has been demonstrated using immunological and—in some cases—clinical endpoints.

Active specific immunotherapy approaches to the treatment of tumors have been widely investigated during recent years. Numerous studies involving the vaccination of patients with their own inactivated tumor cells have been reported. These studies have demonstrated that inclusion of an adjuvant is necessary to stimulate the patient's immune system especially against the autologous, or derived from self, tumor cells. For example, methods utilizing the particulate adjuvant, *Bacillus* Calmette-Guerin (BCG) cells, administered systemically or mixed with the patient's own tumor cells have been shown to induce tumor-specific immunity in laboratory animals. Peters, L. C., Brandhorst, J. S., Hanna Jr., M. G., Preparation of Immuno-Therapeutic Autologous Tumor Cell Vaccines from Solid Tumors; Cancer Res. 39: 1353-1360 (1979).

In another preferred embodiment the dendritic cells used in the aforementioned pharmaceutical or vaccine composition are loaded mature dendritic cells (mDC) which originate from lysate-loaded and further matured immature dendritic cells (iDC) or which were loaded after or during maturation. The term "immature" when used in accordance with the present application relates to professional antigen-presenting cells that are characterized by their ability to take-up and process antigens. The term "mature" when used in accordance with the present application relates to professional antigen-presenting cells that express costimulatory factors and antigens in the context of MHC class molecules or CD1 molecules and can activate T cells, regulatory NKT cells and/or B cells.]

A pharmaceutical or vaccine composition comprising dendritic cells and temperature-induced cell lysates, comprises them preferably as dendritic cells loaded with lysate. Said dendritic cells are preferably loaded in their immature stadium (immature DC) with the cell lysates of the present invention and are subsequently being brought to maturation. Mature DC loaded with the lysate according to the invention are preferably used to treat or prevent tumorous or infectious diseases. In case, the pharmaceutical or vaccine composition is used for vaccination against autoimmune diseases the immature DC are loaded and preferably arrested in their immature stadium to develop tolerance when being administered as already described hereinabove.

Moreover, the present invention relates to a method for the production of a vaccine composition comprising the step of combining a cell lysate obtainable by the process according to the present invention with an adjuvant or with dendritic cells.

The present invention also relates to a method for the production of a pharmaceutical composition comprising the step of combining a cell lysate obtainable by the process according to the present invention with a pharmaceutically acceptable carrier.

In another aspect the present invention relates to a method for the treatment or prevention, e.g. by vaccination, of cancer, tumorous diseases, infections and/or autoimmune diseases in an individual comprising the step of administering to the individual a therapeutically or prophylactically effective amount of the lysate obtainable by the process according to the invention.

In the context of the present invention the term "individual" means a subject in need of a treatment or prevention of cancer, tumorous diseases, infections and/or autoimmune diseases. Preferably, the subject is a vertebrate, even more preferred a mammal, particularly preferred a human.

The term "administered" means administration of a therapeutically or prophylactically effective dose of the cell lysate of the invention to an individual. By "therapeutically or prophylactically effective amount" is meant a dose that produces the effects for which it is administered. The exact dose will depend on the purpose of the treatment, and will be ascertainable by one skilled in the art using known techniques. As is known in the art and described above, adjustments for systemic versus localized delivery, age, body weight, general health, sex, diet, time of administration, drug interaction and the severity of the condition may be necessary, and will be ascertainable with routine experimentation by those skilled in the art.

In accordance with the present invention the term "vaccination" is related to a general process for immunization against cancers, tumorous diseases, infections and/or autoimmune diseases. Vaccination is a form of deliberate artificial immunization whereby the cell lysates or with cell lysate loaded dendritic cells of the present invention are administered. The cell lysates are administered in a form as described herein, supra, and may sensitise the immune system such that if cancer, tumorous diseases, infections and/or autoimmune diseases arise within the body are being treated or prevented. See, for example, Immunology, at pp. 87-88; AMA Encyclopedia of Medicine at 573-574 and 1034; S. J. Cryz, Jr., in Immunotherapy and Vaccines, edited by Stanley J. Cryz, pp. 3-11, VCH, Weinheim, Germany 1991. For an overview of the immune system from a molecular perspective, see, for example, Mary S. Leffell, An Overview of the Immune System: The Molecular Basis for Immune Responses, in Human Immunology Handbook pp. 1-45. Vaccination is also associated with immunization.

Immunization is a general term, and the term vaccination is used when patients are immunized. In general, immunization can be used as a preventive or as a therapeutic treatment. The preventive use of immunization is a prophylactic treatment, whereas the use of immunization while the disease is in progress is immunotherapy. Immunization provides two types of acquired immunity, active and passive. Immunotherapy is the treatment of a disease by immunization, active or passive, or by the use of agents that modify the actions of lymphocytes. In particular, immunotherapy refers to the stimulation of the immune system and conventionally uses a form of immunostimulant, a substance that causes a general, non-specific, stimulation of the immune system. The American Medical Association. Encyclopedia of Medicine, p. 576 (this encyclopedia will hereinafter be referred to as "AMA Encyclopedia of Medicine").

In a method for inducing an immune response to treat or prevent cancer, tumorous diseases, infections and/or autoimmune diseases, one or more cell lysates or with cell lysate loaded dendritic cells according to the invention are provided, and an effective amount of one or more of the cell lysates or with cell lysate loaded dendritic cells are injected at least once so as to permit release of biologically active quantities of the immunostimulant over a period of time to induce an immune response to the presence of active tumor cells.

An individual for the purposes of the present invention includes both humans and other animals, preferably vertebrates and more preferably mammals. Thus the methods are applicable to both human therapy and veterinary applications.

In a preferred embodiment the individual is a mammal, e.g. a mouse, and in a most preferred embodiment the individual is human.

The compounds described herein having the desired therapeutic or prophylactic activity may be administered in a physiologically acceptable carrier to a patient, as described herein. Depending upon the manner of introduction, the compounds may be formulated in a variety of ways as discussed below. The concentration of therapeutically active compound in the formulation may vary from about 0.1-100 wt %. However, it is also envisaged that the person skilled in the art is readily in a position to determine the concentration of the therapeutically active compound in the formulation by using his common general knowledge. The agents maybe administered alone or in combination with other treatments, i.e., radiation, or other chemotherapeutic agents.

In a preferred embodiment, the pharmaceutical compositions are in a water-soluble form, such as pharmaceutically acceptable salts, which is meant to include both acid and base addition salts.

The administration of the candidate agents of the present invention can be done in a variety of ways as discussed above, including, but not limited to, orally, subcutaneously, intravenously, intranasally, transdermally, intranodally, peritumorally, intratumorally, intrarectally, intraperitoneally, intramuscularly, intrapulmonary, vaginally, rectally, or intraocularly. In some instances, for example, in the treatment of wounds and inflammation, the candidate agents may be directly applied as a solution dry spray.

The cell lysates that are obtainable by the aforementioned processes can be administered to the subject at a suitable dose. Administration of the suitable compositions may be effected by different ways, e.g., by intravenous, intraperitoneal, subcutaneous, intramuscular, topical, intradermal, intranasal, intranodal, intrarectal, peritumotal, intratumoral or intrabronchial administration. The attending physician and clinical factors will determine the dosage regimen. As is well known in the medical arts, dosages for any one patient depends upon many factors, including the patient's size, body surface area, age, the particular compound to be administered, sex, time and route of administration, general health, and other drugs being administered concurrently. A typical dose of lysate can origin from about 1000 to $10^{13}$ cells and the typical dose for dendritic cells is about $10^4$ to $10^{12}$ cells, however, doses below and above this exemplary range are envisaged. Preferably, the dose of lysate corresponds to amounts generated from cells numbers between $10^4$ to $10^{12}$ cells, more preferably between $10^5$ to $10^{11}$ cells, more preferably between $10^6$ to $10^{10}$ cells. Preferably, the dose for loaded dendritic cells is between $10^5$ to $10^{11}$ cells, more preferably between $10^6$ to $10^9$ cells. Doses can vary between individuals and can be split to multiple injections at different sites and/or administration routes. Suitable and optimal doses can be determined by those skilled in the art. The amount of cell lysate used for loading dendritic cells can be determined by those skilled in the art, for example by those in vitro and or in vivo assays which are exemplary shown in the examples. Preferable amounts for lysates originate from $10^3$ to $10^{13}$ cells, more preamble from $10^4$ to $10^{12}$ cells, more preferable from $10^5$ to $10^{11}$ cells, and more preferably from $10^6$ to $10^{10}$ cells. Generally, the regimen as a regular administration of the pharmaceutical or vaccine composition should be in the range of 0.1 µg to 10 g per dose for the lysates, preferably 50 to 100 mg, amounts for fractionated lysates can be correspondently lower but may reach the high amounts. The dosages are preferably given once a week, however, during progression of the treatment the dosages can be given in much longer time intervals and in need can be given in much shorter time intervals, e.g., daily. In a preferred case the immune response is monitored using herein described methods and further methods known to those skilled in the art and dosages are optimized, e.g., in time, amount and/or composition.

If the regimen is a continuous infusion, it should also be in the range of 0.1 µg to 10 mg per kilogram of body weight per minute, respectively. Progress can be monitored by periodic assessment. The cell lysates of the invention may be administered locally or systemically. Administration will preferably be parenterally, e.g., intravenously, intranodally, intra peritoneally, intra tumourally, peri tumorally. Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

It is also envisaged that the cell lysates are employed in co-therapy approaches, i.e. in co-administration with other medicaments or drugs, for example anti-cancer drugs.

When vaccine therapy is carried out using the cell lysates or with cell lysate loaded dendritic cells of the present invention, they may be administered only once. However, it is desirable to repeat the administration to the same site of a body to achieve coexistence of a tumor antigen and a cytokine or a cytokine-inducing agent as long as possible. For example, both components may preferably coexist for 3 hours or more so that inflammatory reaction at the site of administration can be induced and conditions can be achieved wherein immune cells are concentrated and cells are kept at the site. When a cell lysate without adjuvant is administered, an adjuvant may be administered to the same site. Generally, the cell lysate can be administered to a patient from which the tumor material is derived; however, the vaccine can also be administered to a patient bearing a tumor that contains, from a viewpoint of pathological diagnosis, the same or relative species of a tumor antigen as that contained in the tumor material. The site to be administered is not particularly limited. Preferred sites include those where cytokines are hardly be diffused and disappeared, for example, intradermal, subcutaneous or intramuscular sites, in lymphnodes, and in a main organ such as spleen. However, by choosing a dosage form, which prevents ready diffusion of the active ingredients of the tumor vaccine, local administrations may sometimes be performable to any site of a body, or by applying a drug delivery system, the systemic administration may sometimes be possible. The dose and administration period of the tumor vaccine of the present invention are not particularly limited. It is desirable to determine an appropriate dose and administration period by observing effects of the vaccine therapy. The administration can be made, for example, by injections and the like.

It is also preferred that the cell lysates or with cell lysate loaded dendritic cells are administered to an individual for the treatment or prevention of against infections, e.g. caused by microorganisms like bacteria, fungi, viruses and/or parasites or autoimmune diseases. An autoimmune disease may arise from immune recognition and reaction against the individual's own cells or parts of the own body. Another preferred embodiment for vaccination is a combination of an immunization with dendritic cells loaded a cell lysate according to the present invention followed by boosting with the necrotic cell lysate.

According to the present invention, the tumor cell lysates, which are used for the preparation of a pharmaceutical or vaccine composition, can either be autologous or allogeneic or xenogenic with respect to the treated individual. It is also envisaged that the tumor cell lysates can be obtained from a tumor/tumor cell material/metastasis and used for the preparation of a pharmaceutical or vaccine composition or cell lines, including cell lines, e.g., tumor cell lines, or primary cell lines or cell lines or cultures from primary material and the like administered for treating or preventing another kind of tumor. For example tumor cells derived from leukaemias or lymphomas can be used to treat or prevent colon carcinoma. In another preferred embodiment of the present invention the pharmaceutical or vaccine composition used for the vaccination comprises one or more tumor cell lysates produced from different tumors/tumor material/tumor cells in order to avoid a so-called tumor escape. These lysates can be loaded to dendritic cells or their precursor states as described above and used as such as a component of vaccine or pharmaceutical compositions for administration.

Additionally, it is preferred that infected tumor cells as described hereinabove are used for vaccination against infections, whereby the infectious component harboured by the infected cells may be additionally inactivated by chemical or physical means. It is also envisaged that non-infectious variants or mutants of the infectious component are needed for infecting said tumor cells.

The invention also relates to the use of the lysate obtainable by the process according to the invention for the preparation of a vaccine or pharmaceutical composition for the treatment or prevention of cancer, tumorous diseases, infections and/or autoimmune diseases.

In a preferred embodiment the cancer or tumorous disease to be treated or prevented is a cancer/tumorous disease of the head and neck, lung, mediastinum, gastrointestinal tract, genitourinary system, gynaecological system, breast, endocrine system, skin, childhood, unknown primary site or metastatic cancer, a sarcoma of the soft tissue and bone, a mesothelioma, a melanoma, a neoplasm of the central nervous system, a lymphoma, a leukaemia, a paraneoplastic syndrome, a peritoneal carcinomastosis, a immunosuppression-related malignancy and/or metastatic cancer. However, said cancer/tumorous disease may also be selected from those mentioned hereinabove in connection with the process according to the invention.

The infection to be treated or prevented is preferably bacterial infection, viral infection, fungal infection, protozoal infection and/or helminthic infection. More preferably the bacterial infection, viral infection, fungal infection, protozoal infection and/or helminthic infection is selected from the group consisting of bacterial infections like sepsis and sepsis shock, fever of unknown origin, infective endocarditis, intraabdominal infections and abscesses, acute infectious, diarrheal diseases and bacterial food poisoning, sexually transmitted diseases, pelvic inflammatory disease, urinary tract infections and pyelonephritis, osteomyelitis, infections of the skin, muscle, and soft tissues, infections in injection drug users, Infections from bites, scratches, and burns, infections in transplant recipients and hospital-acquired and intravascular device-related infections. More preferably the infection to be treated or prevented is selected from the group consisting of bacterial infections like pneumococcal infections, staphylococcal infections, streptococcal and enterococcal infections, diphtheria, other corynebacterial infections and anthrax, listeria monocytogenes infections, clostridial infections, like tetanus, botulism, gas gangrene, antibiotic-assiociated colits, meningococcal infections, gonococcal infections, *moraxella* (*branhamella*) *catarrhalis*, other *moraxella* species, and *kingella* infections, *Haemophilus* infections caused by *haemophilus* species, the HACEK group and other gram-negative *bacilli* infections, *legionella* infections, pertussis infections, gram-negative enteric *bacilli* infections, *helicobacter* infections, *pseudomonas* species and related organisms infections, *salmonella* infections, *shigella* infections, *campylobacter* and related species infections, cholera and other vibrio infections, *brucella* infections, tularaemia infections, plague and other *yersinia* infections, bartonella infections, including cat-scratch disease, donovanosis (Granuloma Inguinale) infections, nocardiosis, actinomycosis, infections due to mixed anaerobic organism, tuberculosis, leprosy (Hanses's Disease), infections due to nontuberculous mycobacteria, syphilis, endemic treponematoses, leptospirosis, relapsing fever, lyme borreliosis, rickettsial diseases, mycoplasma infections, chlamydial infections, viral infections due to Herpes simple viruses, Varicella-zoster virus infections, Epstein-barr virus infections, including infectious mononucleosis, Cytomegalovirus and human herpesvirus types 6, 7, and 8 infections, smallpox, vaccinia, and other poxviruses infections, parvovirus inactions, Human papillomavirus infections, common viral respiratory infections, influenzy, viral gastroenteritis, enteroviruses and reoviruses infections, measles, rubelly (German measles), mumps, rabies virus and other rhabdoviruses infections, infections caused by arthropod- and rodent-borne viruses, Marburg and ebola viruses (Filoviridae), fungal infections like histoplasmosis, coccidioidomycosis, blastomycosis, cryptococcosis, candidiasis, aspergillosis, mucormycosis, miscellaneous mycoses and prototheca infections, Pneumocystic carinii infection, protozoal infections like amebiasis and infection with free-living amebas, malaria and other diseases caused by red blood cell parasites, leishmaniasis, trypanosomiasis, Toxoplasma infection, protozoal intestinal infections and trichomoniasis, heiminthic infections, like trichinosis and infections with other tissue nematodes, Intestinal nematodes, filariasis and related infections (Loiasis, Onchocerciasis, and Dracunculiasis), schistosomiasis and other trematode infections or Cestodes infections.

The autoimmune disease to be treated or prevented is preferably selected from the group consisting of allergic encephalomyelitis, autoimmune haemolytic anemia, autoimmune thyroiditis, Hashimoto's disease, autoimmune male infertility, bullous pemphigoid, Celiac disease, Grave's disease, Goodpasture's syndrome, idiopathic thrombocytopenic purpura, insulin-resistant diabetis mellitus, myasthenia gravis, pernicious anemia, pemphigus vulgaris, polyarteritis nodosa, primary biliary cirrhosis, Reiter's disease, rheumatic fever, sarcoidosis, Sjogren's disease, systemic lupus erythematosus, sympathetic ophthalmia, multiple sclerosis and/or viral myocarditis by Cocksakie B virus response.

In view of the in vivo and in vitro results of the examples of the present invention it is expected that the invention provides an advantageous cancer, tumorous disease, infection and/or autoimmune disease vaccine. In particular, mice developed both a humoral and cellular immune response when challenged with tumor antigens present in/on tumor cells, which served as a source for the produced cell lysate. Moreover, even antibodies against carbohydrate antigens have been developed which has not or rarely been observed so far when conventionally produced tumor cell lysates have been administered. Additionally, it was found that mice with an implemented human immune system showed the same phenomenon.

The Figures show:

FIG. 1 Analysis of propidium iodide and annexin V-FITC labelled temperature induced NM-F9 tumor cells (A-D) and anti-Hsp70 labeled NM-F9 tumor cells by flow cytometry.

Figure 2:
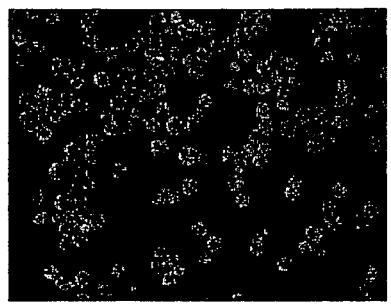
Figure 2:
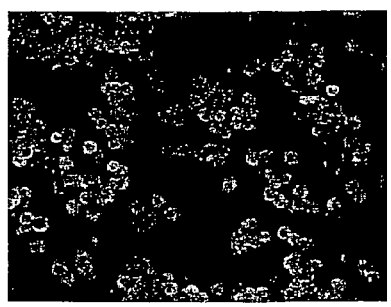
Figure 2:
Figure 3:
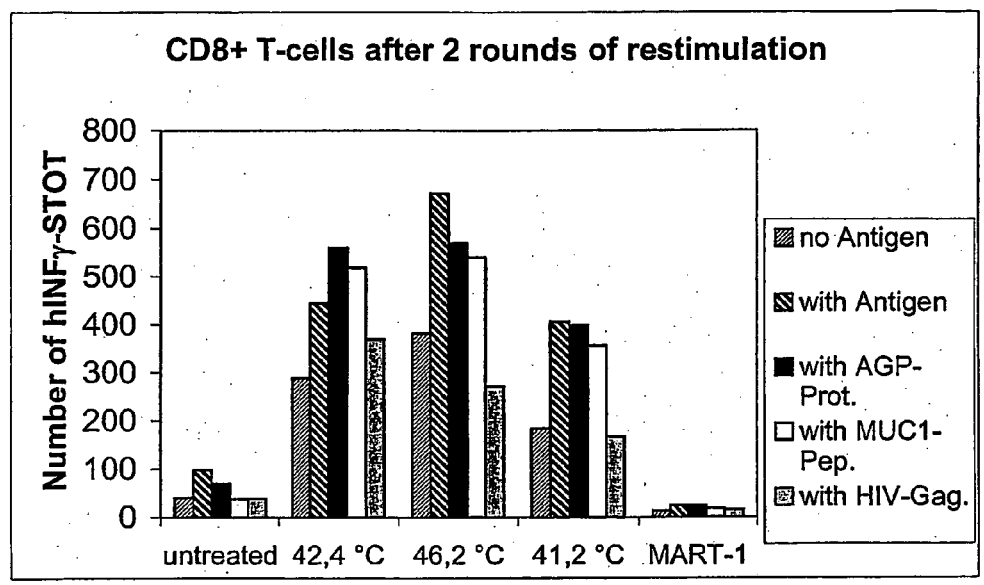
Figure 4:
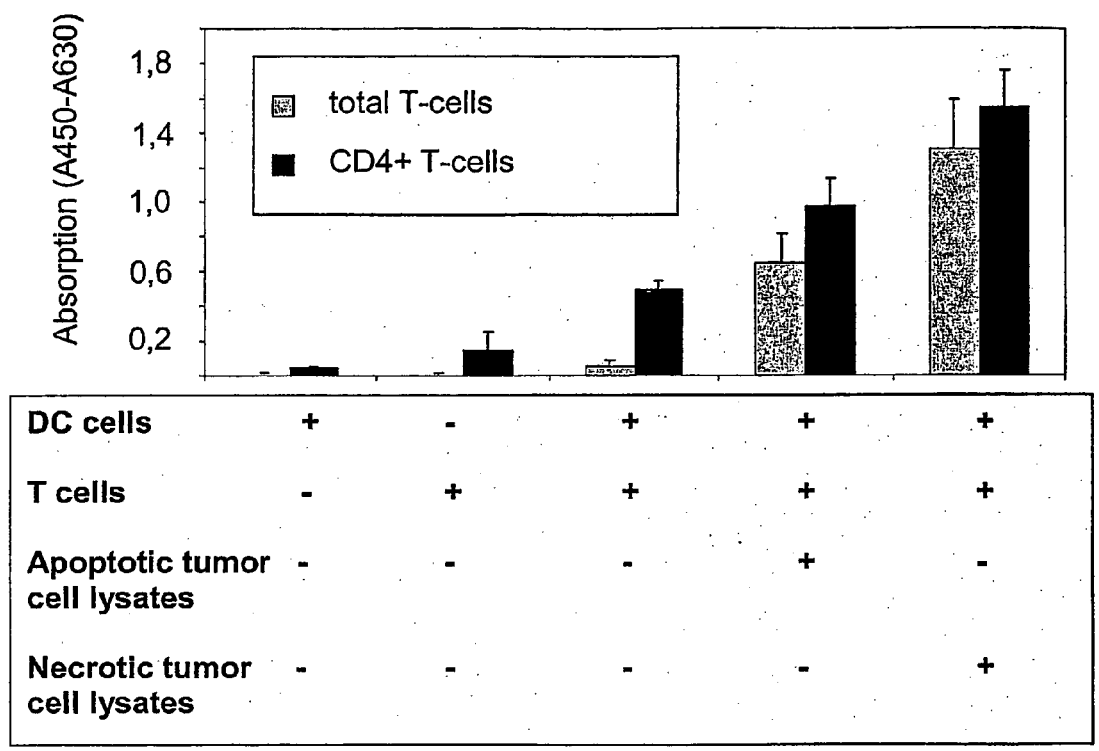

FIG. 2 Detection of cellular Hsp 70 expression in temperature treated NM-F9 tumour cells derived from K562 tumor cells by immunocytochemical staining; panel a) shows NM-F9 cells incubated at 41.2° C., the staining of Hsp70 positive cells was done by using a secondary Cy3-labelled antibody; panel b) shows NM-F9 cells incubated at 46.2° C. in the dark field control; panel c) shows the same NM-F9 cells incubated at 46.2° C., wherein Hsp70 positive cells are labeled with a secondary Cy3-labelld antibody FIG. 3 In vitro analysis of T cell (CD8) stimulation by temperature treated NM-F9 tumor cell lysate loaded dendritic cells FIG. 4 In vitro analysis of T cell (CD4) activation by mature dendritic cells which were incubated with different NM-F9 tumor lysates.

Figure 5:
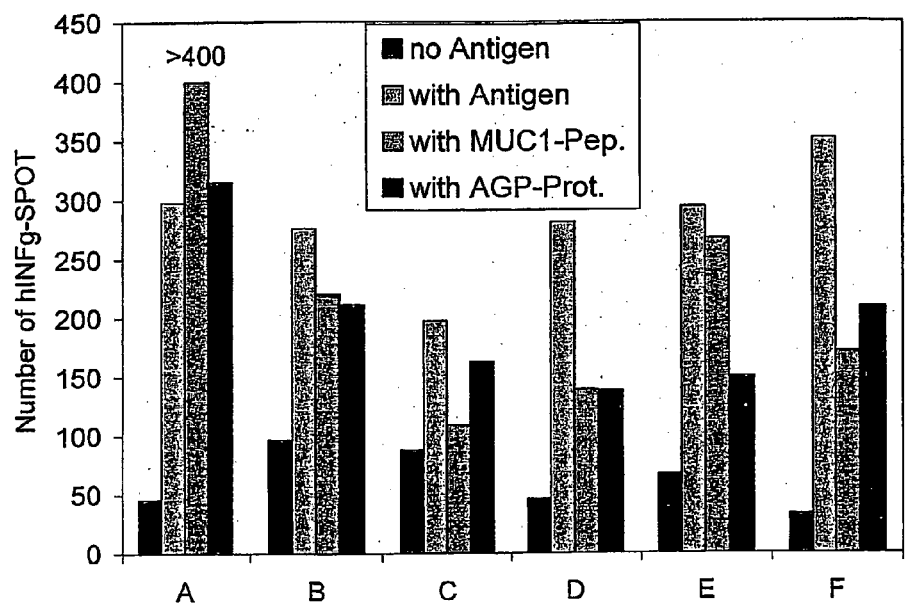

FIG. 5 In vitro induction of CD8+ T-cell responses with various necrotic NM-F9 cell lysates after one stimulation.

The tables show:

TABLE 1

Induction of apoptosis, necrosis and expression of membrane bound HSP 70 protein on NM-F9 tumor cells derived from K562 by temperature treatment.

| temperature | Percent of total (%) | | | |
| --- | --- | --- | --- | --- |
| | cells | Apoptotic cells | Necrotic cells | Hsp 70 positive cells |
| 37.0° C. | 70 +/− 3.7 | 21 +/− 1.9 | 9 +/− 3.2 | 5 |
| 38.0° C. | 64 | 25 | 9 | 1 |
| 40.0° C. | 48 | 40 | 12 | 3 |
| 41.2° C. | 44 | 40 | 15 | 33 |
| 42.0° C. | 34 | 45 | 20 | 1 |
| 42.4° C. | 25 +/− 10 | 59 +/− 11 | 16 +/− 0.35 | 1 |
| 43.0° C. | 34 | 47 | 19 | 0.7 |
| 44.0° C. | 25 | 52 | 23 | 10 |
| 46.2° C. | 5 +/− 0.6 | 9 +/− 0.2 | 86 +/− 0.7 | 5 |

TABLE 2

Humoral immune response in NMRI mice induced by temperature pre-treated NM-F9 tumor cell lysates.

| Vaccine | Number of mice with antigen specific IgG immune response/total number | | | |
| --- | --- | --- | --- | --- |
| | AGP | TF | Tn | MUC1 |
| Necrotic tumor cell lysate 46.2° C. | 2/3 | 3/3 | 3/3 | 3/3 |
| Apoptotic tumor cell lysate 42.4° C. | 2/3 | 0/3 | 0/3 | 1/3 |
| Lysate of tumor cells with increased HSP70 expression 41.2° C. | 0/3 | 0/3 | 0/3 | 0/3 |
| Lysate of untreated tumor cells 37° C. | 2/3 | 0/3 | 0/3 | 0/3 |

TABLE 3

Humoral immune response in NOD/SCID mice induced by temperature pre-treated NM-F9 tumor cells lysates.

| Vaccine | Number of mice with antigen specific IgG immune response/total number | | | |
|---|---|---|---|---|
| | AGP | TF | Tn | MUC1 |
| Necrotic tumor cell lysate 46.2° C. | 3/3 | 3/3 | 3/3 | 3/3 |
| Apoptotic tumor cell lysate 42.4° C. | 1/3 | 1/3 | 1/3 | 0/3 |
| Lysate of tumor cells with increased HSP 70 expression 41.2° C. | 0/3 | 0/3 | 0/3 | 0/3 |
| Lysate of untreated cells 37° C. | 0/3 | 1/3 | 1/3 | 0/3 |
| Negative control, Mel624 cell lysate, AGP-, TF-, Tn-, MUC1- | 0/3 | 0/3 | 0/3 | 0/3 |

The examples illustrate the invention.

1. Process of Temperature Treatment for Preparation of Apoptotic and Necrotic Tumor Cell Lysate In the following Example K562 cells (ATCC: CCL-243) may be used. However, preferably TF-positive F9 cells (NM-F9) derived from K562 tumor cells (ATCC: CCL-243) are used which were cultivated in RPMI media with 10% FCS, 1% glutamic acid (complete RPMI media), 8% $CO_2$, 95% humidity at 37° C. For each preparation $7.5 \times 10^5$ K562-cells were harvested. Before temperature induction tumor cells were resuspended in 450 microliter complete RPMI media (for mouse vaccination, section 5) or in serum-free AIMV-media (for in vitro assay, section 4). For temperature induction four aliquots of 100 microliter and one aliquot of 50 microliter (0.5 ml e-cups) of the tumor cells were incubated for 2 h in a preheated thermocycler (Eppendorf, Hamburg, Germany). Afterwards temperature treated cells were resuspended in 25 ml complete RPMI media or AIMV media and recultured under conditions above (in complete RPMI media at 37° C.). For induction of apoptosis and necrosis an incubation time of 22 h found to be better than 6 h and 14.5 h (results described in section 2, flow cytometry). Before lysis, tumor cells were washed with PBS (for mouse vaccination) or AIMV (for in vitro assay) three times. Afterwards cell counts were adjusted to $5 \times 10^6$ cells/75 microliter PBS (for mouse vaccination) or $1 \times 10^6$/500 microliter AIMV (for in vitro assay). Cell lysis was performed by freezing in liquid nitrogen and thawing at 37° C. (water bath) for three cycles (30 sec/phase in liquid nitrogen). Cells lysates were stored at −80° C.

To improve the immunogenity and to simplify the induction process for preparing necrotic cells, the duration of temperature induction (2 h or 3 h) as well as the reculture time at 37° C. (0 h, 3 h, 22 h) were varied. In these experiments temperature induction occurred in PBS or serum-free AIMV media in a thermoblock at 46.5° C. Heat-treated cells were recultured in the same volume and media in microcentrifuge tubes in which temperature induction had taken place. Necrotic cell lysate (in AIMV-media) was used for in vitro analysis (FIG. 5). The following preparations were lysed by freezing and thawing: 1) Temperature induction 2 h (sample A) and 3 h (sample B) without reculture time. 2) Temperature induction 2 h (sample C) and 3 h (sample D) and 3 h reculture time. 3) Temperature induction 2 h and 22 h reculture time in microcentrifuge tubes (sample E). 4) as control: Temperature induction 2 h and 22 h reculture time resuspended media.

2. Determination of Vital, Apoptotic and Necrotic Cells by Flow Cytometry

For determination of vital, apoptotic and necrotic cells the Apoptosis Detection Kit I (Pharmingen, Heidelberg, Germany) containing Annexin V-FITC and Propidium iodide was used; Apoptotic cells were only stained by Annexin V-FITC, necrotic cells were stained by Annexin V-FITC and Propidium iodide (PI). For analysis. $3 \times 10^5$ heat-treated and recultured K562 cells (ATCC: CCL-243) may be used. However, TF-positive F9 cells derived from K562 tumor cells (NM-F9) ( ) were used which were harvested and washed in PBS twice. Cell pellets were resuspended in 1× binding buffer (10 mM Hepes pH 7.4, 140 mM NaCl and 2.5 mM CaCl 2) and stained with 5 microliter Annexin V-FITC and 2 microliter PI. After 15 min incubation time at room temperature (in a dark place) samples were diluted in 400 microliter 1× binding buffer. For flow cytometric analysis the flow cytometer Coulter Epics XL of Beckman-Coulter (Miami, USA) with Expo 32 ADC software (Beckman-Coulter) was used. For investigation the following parameter were used:

"sideward scatter": 807 volt, "gain" 5, forward scatter": 26 volt "gain" 1.

Annexin V: FL1-channel, 707 volt, "gain" 1, compensation FL1-FL3 0.4.

PI: FL3-channel, 729 volt, "gain" 1, compensation FL3-FL1 17.9.

Proportional determination of vital, necrotic and apoptotic cells of heat-treated 22 h recultured TF-positive F9 cells derived from K562 cells (NM-F9) are described in "dot plots" diagrams in FIG. 1. K562-tumor cells were incubated in a thermocycler for 2 h at 37° C. (control, FIG. 1A), at 42.4° C. (FIG. 1B) and at 46.2° C. (FIG. 1C). After temperature induction cells were recultured 22 h at 37° C.

In a "dot plot" diagram the fluorescence intensity of Annex in V-FITC/PI stained cells is described by the position of spots in the coordinate field. The coordinate field is separated into quadrants, whose position is determined by negative and positive control using of PI or Annexin V-FITC stained cells. The unstained population in the left quadrant below represents the vital cells (no dye can enter the cell), the population in the right quadrant below represents the apoptotic cells (only Annexin V-FITC can enter the cell) and the population in the upper left and right quadrant represents the necrotic cells.

To determine the best temperature for induction of apoptosis and necrosis, TF-positive F9 cells derived from K562-cells were incubated for 2 h at 10 different temperatures described in table 1. As shown in FIGS. 1B and C the optimal temperature for induction of apoptotic cells is 42.4° C. and the temperature for induction of necrotic cells is 46.2° C.

3. Preparation of Tumor Cell Lysate with High Expression of Membrane Bound HSP 70 Proteins In the following Example K562 cells (ATCC: CCL-243) may be used. However, TF-positive F9 cells derived from K562 (NM-F9) are preferably used. With the latter cells it was observed that the preparation of heat-treated TF-positive F9 cells derived from K562 (NM-F9) tumor cell lysate with high expression of membrane bound HSP 70 is comparable to the preparation of necrotic and apoptotic cells. The optimal reculture time for TF-positive F9 cells derived from K562 cells (NM-F9) expressing high amounts of HSP 70 were 14.5 h (results, section 4).

Detection of Membrane Bound HSP 70 Protein by Flow Cytometry $3 \times 10^5$ TF-positive F9 cells derived from K562 cells (NM-F9) which are preferably used were harvested and resuspended in 25 microliter complete RPMI media. After 45 min incubation with anti-human HSP 70-IgG1 antibody (1:100 diluted in complete RPMI) at 4° C., cells were washed in PBS/10% FCS twice (5 min centrifugation at 1500 upm, Heraeus Multifuge). Afterwards the cells were incubated for 30 min with a secondary Cy3-anti-mouse-IgG antibody at 4° C. (1:200 diluted in PBS, Dianova, Hamburg, Germany). The cells were washed in PBS twice and resuspended in 200 microliter PBS. For analysis the following parameters were used: "sideward scatter" and "forward scatter" as already-described.

Cy3: FL2-chanel, 740 volt, "gain" 1.

The results are described in the overlay-histogram (FIG. 1D), which show HSP 70 induction of the control (incubated at 37° C.) and F9cells incubated at 41.2° C. As seen in the histogram in about 33% of the F9cell population incubated at 41.2° C. the expression of HSP 70 proteins is increased.

The HSP 70 expression of TF-positive F9 cells derived from K562 cells (NM-F9) incubated for 2 h at 10 different temperatures is described in table 1. The optimal HSP 70 expression in heat-treated TF-positive F9 cells derived from K562 cells (NM-F9) is received by temperature induction at 41.2° C. and 14.5 h recultured at 37° C.

Detection of Cellular HSP 70 Expression by Immunocytochemistry

The staining process occurred in a humid chamber.

For coating the slide $5 \times 10^4$ cells in 50 microliter were dropped on the slide (in a humid chamber), 30 min incubated at 37° C. in the $CO_2$ incubator and 1 h incubated at room temperature. After removing the supernatant the samples were dried for 15 min at room temperature and stored at −20° C. wrapped in aluminium foil. After thawing the cells were fixed in 5% formaldehyde (diluted in PBS, 5 min incubated at room temperature). The cells were washed in PBS three times and blocked by incubating 1 h with 5% BSA/PBS. After washing in PBS cells were labelled by anti-HSP 70 antibody (as above, 1:200 diluted in 1% BSA/PBS, 90 min incubation at RT). After washing the cells with PBS three times K562 cells were incubated for 1 h with secondary Cy3-anti-mouse IgG antibody (1:200 diluted in 1% BSA/PBS) at room temperature. Finally the cells were embedded in Mowiol-solution (6 g glycerin, 2.4 g mowiol 4-88 (Calbiochem, Bad Soden, Germany), 6 ml $H_2O$, 12 ml 0.2 M Tris-HCl pH 8.5 mixing 2 h at RT, 15 min centrifugation at 5000×g, addition of Diazobizyclooctan (Sigma)). Immunochemical analysis was performed with a by Zeiss Microskope Axioplan (Oberkochen, Germany). The results of cellular HSP 70—expression by F9 incubated at 41.2° C., incubated at 42.4° C. (apoptotic cells) and incubated at 46.2° C. (necrotic cells) is shown in FIG. 2. 80-90% of K562 cells incubated at 41.2° C. have increased HSP 70 expression. In contrast 2-5% of necrotic cells incubated at 46.2° C. showed increased HSP 70 expression.

For immunogenity studies lysates of four differently treated cell populations were prepared.

1) lysate of necrotic TF-positive F9 cells derived from K562 cells (NM-F9) (2 h temperature induction at 46.2° C., 22 h recultured at 37° C.), 2) lysate of apoptotic TF-positive F9 cells derived from K562 cells (2 h temperature induction at 42.4° C., 22 h recultured at 37° C.), 3) lysate of TF-positive F9 cells derived from K562 cells (NM-F9) with increased expression of HSP 70, (2 h temperature induction at 41.2° C., 14.5 h recultured at 37° C.), 4) lysate of untreated TF-positive F9 cells derived from K562 cells (incubated at 37° C.).

4. Specific Activation of Cb8+ and CD4+ T-Cells by Heat Treated Tumor Cell Lysate Taken Up, Processed and Presented by Dendritic Cells Dendritic cells can be incubated with K562 cells, however, are preferably incubated with different TF-positive F9 cells (NM-F9) derived from K562 tumor lysates overnight. After phagocytosis of TF-positive F9 cells derived from K562 lysates the maturation of dendritic cells was induced. Afterwards the activation of CD8+ (FIG. 3) and CD4+ (FIG. 4) T-cells by mature dendritic cells was analysed and the dendritic cells were incubated with CD8+ and in order to stimulate these cells in an antigene-specific manner.

Preparation of Immature Human Dendritic Cells

Immature human dendritic cells were prepared by differentiation of human monocytes (hmoDC) by the method of Romani (Romani N et al. 1994, J. Exp. Med. 180: 83-93). Peripheral blood monocytes were isolated from peripheral blood of healthy human donor by Ficoll gradient centrifugation. Adherent cells which adhere on plastic were cultured for 6 days in RPMI-1640, 10% FCS, 1000 U/ml GM-CSF 2.5 ng/ml TNFα and 1000 U/m IL-4.

Secondly immature dendritic cells were prepared (Nemod-iDC, which are optimized MUTZ-3 derived immature dendritic cells as described in WO 03/023023 which can be purchased from NEMOD Immuntherapie AG, Robert-Rössle-Strasse 10, D-13125 Berlin, Germany)); from a human cell line according to the methods described in WO 03/023023

Loading and Maturation of Nemod-iDC

The immature hmoDC or Nemod-iDC. ($10^6$ cells/sample) were incubated overnight with tumor cell lysates at a proportion of 1:1. After washing the dendritic cells with sterile PBS GM-CSF, IL-4 and 75 ng/ml TNFα were added. The mature hmoDC, Nemod-mDC became CD14−, CD1a+, CD80hi, CD86hi, CD40hi, MHCIIhi, CD83hi, DC-Sign+ (flow cytometry, suffix: −=no expression, hi=high expression, +=positive expression). Prior to T cell sensitisation, the antigen loaded Nemod-mDC were irradiated with 30 Gy.

Preparation of Peripheral Blood T-Cells

T cells were isolated from the non-adherent fraction of PBMC of healthy HLA-A2 positive donor by a column of nylon wool (Polysciences Inc., Eppelheim, Ger). Alternativaly CD4+ or CD8+-T-cells were isolated from PBMC by CD4- or CD8-T-cell-MACS-Isolationkits (Miltenyi Biotec, Köln, Ger).

Induction of Tumor Cell Lysate Specific T-Cells

Total T-cells, CD4+ or CD8+ T-cells were incubated in serum-free media (AIM-V medium) with mature hmoDC or Nemod-mDC loaded with cell lysate in serum. The ratio of responder: stimulator (T-cell: DC) was 10-20:1. After overnight incubation 10 U/ml IL-2, 1.5 U/ml IL-1β and 5 ng/ml IL-7 were added. After incubation for four days T-cells were restimulated by mature hmoDC or Nemod-mDC loaded with antigen. T-cells were analysed by IFNγ-ELISPOT Assay (FIGS. 3 and 5) following overnight incubation or after 4 days (without addition of cytokine) the cell proliferation was analysed by BrdU assay (FIG. 4).

IFNγ-ELISPOT Assay

ELISPOT analysis was performed using a kit (Mabtech, Nacka, Sweden) and PVDF-bottomed 96-well-Multiscreen plates from Millipore (Bedford, USA). Before coating overnight with mouse-anti-human-IFNγ antibodies (15 microgram/ml, at 4° C.) PVDF was soaked with 70% ethanol (50 microliter/well). After washing with PBS, $7 \times 10^4$ T-cells together with the relevant number of antigen-loaded mature hmoDC or Nemod-mDC in 200 microliter medium/well were incubated 16 h at 37° C. Cells were then removed and plates washed three times with PBS/Tween. Secreted IFNγ was detected by incubating with biotinylated anti-human-IFNγ antibody (50 microliter/well in PBS, 2 h, RT), followed by a conjugate of streptavidin alkaline phosphatase (1:1000 dilution, 100 microliter/well, 1 h incubation at RT). After washing with PBS-Tween four times, detection of alkaline phosphatase was achieved by staining with BCIP (35 microliter/10 ml detection buffer) and NBT (45 microliter/10 ml detection buffer). The reaction was stopped by water. Prior to analysis with an ELISPOT Reader (Autoimmun Diagnostika GmbH, Strassberg, Germany) 96-well plates were dried for 1 h at 40° C.

T-Cell-Proliferation Assay (BrdU Incorparation)

BrdU was incorporated into proliferating T cells in accordance with the manufacture's protocol. After fixing, the cells were incubated with POD labelled anti-BrdU-antibody. The subsequent staining reaction was stopped by 1M sulfuric acid. Detection of antibody labelling was achieved by photometry at an optical density of 450 nm (Ref. 690 nm).

Results of In Vitro Analysis

In vitro experiments revealed that the immunogenity of tumor cell lysates was improved by heat pretreatment (FIGS. 3, 4 and 5). The best results were achieved by temperature induction at 46.2° C. (about 80% necrotic cells). This result was unexpected. In contrast to many authors preparing necrotic cells by lysing untreated cells (Gallucci, S. Nature Medicine 1999; Kotera, Y. Cancer Res. 2001; Restifo, N.P. Curr. Opin. Immunol. 2000; Sauter, B. J. et al. Exp. Med. 2000) we improved the immunogenity by temperature-induced necrosis of cells prior to lysis. In disagreement with other authors (Dressel (2000), loc. cit; Feng (2001), loc cit.; Melcher (1998), loc. cit; Todryk (2000), loc. cit.) we could not improve the immunogenity by increasing the expression of HSP 70 proteins (temperature induction at 41.2° C.) (FIGS. 3 and 4). As described in table 1 HSP 70 expression as determined by flow cytometry, was increased by temperature induction at 41.2° C. In both heat-induced necrotic cells (46.2° C.) and apoptotic cells (42.4° C.) the surface HSP 70 expression was reduced (necrotic cells) or unchanged (apoptotic cells) (table 1). These results were confirmed by immunofluorescence tests (FIG. 2, 2-5% of necrotic cells (46.2° C.) HSP 70 positive, 80-90% of cells incubated at 41.2° C. HSP 70 positive).

The highest cellular immunogenity (cytotoxic CD8+ T cells and CD4+ T helper cells) was achieved by temperature-induced necrotic cell lysates. Compared to lysates of untreated cells, cell lysates of temperature induced apoptotic cells also induced an improved CD8+ T cell immune response (FIG. 3). An improved cellular immune response was induced in the autologous system (hmoDC) as well as in the semi-allogeneic system (NemodDC). A strong immune response is based on CD8+ and CD4+ T cell activation. Therefore, development of tumor vaccines based on tumor cell lysates can be improved by using temperature-induced necrotic cell lysates. To simplify the process and to improve the immunogenity the preparation process of temperature-induced necrotic cells was optimised. All necrotic TF-positive F9 cells derived from K562 tumor cells (NM-F9) induced by a variety of preparation process (mentioned in section 1) show high immunogenity in "in vitro assay" (FIG. 5). Necrotic cell lysates induced by 2 h incubation at 46.5° C. without reculture (section 1, sample A) induced a small increase in CD8+ T-cell reaction.

5. Vaccination of Mice by Temperature Treated Human Tumor Cell Lysine a) "normal" NMRI mice NMRI mice were vaccinated subcutaneously with lysates of temperature-treated tumor cells ($5 \times 10^6$ cells/mouse) of K562 derived F9 cells (NM-F9). After two weeks mice were boosted with the same tumor vaccine. No tumor growth or other side effects were observed during the vaccination period. One day before immunisation and 9 and 27 days after immunisation mice were bled to analyse serum for: TF-, Tn-, MUC 1- and asialoglycophorin A antibodies by ELISA. For these analyses, 96-well plates were coated with Thomsen-Friedenreich-disaccharide-polyacrylamide-conjugate (TF-PAA), Tn-monosaccharide-PAA-conjugate (Synthesome, Munich, Germany), asialoglycophorin A (AGPA, Sigma) (2 microgram/ml in 50 microliter PBS) and MUC 1 (diluted 1:40 in PBS, optimal dilution was determined by anti-MUC1-antibody A76-A/C7) purified from supernatant of tumor bells as described in PCT/EP03/08014 (After incubation overnight at 4° C. 96-well plates were washed with 0.05% Tween 20 in PBS (washing buffer), blocked with 5% BSA, 0.05% Tween 20 in PBS (1.5 h incubation at RT) and washed again in washing buffer three times. The coated 96-well plates were incubated with different dilutions of mice sera for 2 h at room temperature. The purified antibodies A76-A/C7, A78-G/A7 (Cao (1997), Virchows Arch. 431, 159-166) and Tn-HB1 (diluted 1:500, Dako, Hamburg, Germany) were used as positive controls. For negative control the primary antibody was replaced by medium. After washing in washing buffer three times plates were incubated with peroxidase labelled anti-mouse IgG or IgM (isolated from rabbit, diluted 1:5000, Dianova). Finally plates were washed with washing buffer twice and with PBS one time. The ELISA was developed with 0.4 mg/ml o-phenyldiamine (Sigma) in 25 mM citrate-phosphate buffer pH 5.0 with 0.04% $H_2O_2$ at room temperature (in the dark). The colour reaction was stopped by addition of 2.5 N sulfuric acid (final concentration 0.07 N) and analysed by ELISA-reader at 490 nm (reference filter at 630 nm)

b) Specific activation of human IgG antibody immune response in NOD/SCID mouse model by vaccination of different temperature pre-treated tumor cell lysate NOD-SCID mice provide a commonly used mouse model, popular because of their deficient immune system. In these mice the human immune system is established by intraperitoneal application of human peripheral blood lymphocytes into mice irradiated one day earlier (PBL, standard preparation, $5 \times 10^7$ cell/mouse). 2-4 h after application of PBL, mice were vaccinated subcutaneously with tumor cell lysates of untreated, apoptotic, necrotic or HSP70 expressing cells as an emulsion with incomplete Freund's adjuvant ($5 \times 10^6$ cells/mouse, cells+adjuvant=100 microliter). After 14 days mice were boosted by the same cell lysates. Cell lysates of MeI624 cells ($5 \times 10^6$ cells/mouse) were used as negative control. There was no evidence of tumor growth or other side effects in NOD-SCID mice. For analysis of serum, mice were bled at days 13 and 28 after the first immunisation. The analyses were carried out by ELISA as described above, here the dilution of secondary POD labelled anti human IgG antibody was 1:10 000.

Results of In Vivo Analysis

A humoral IgG immune response against all tested antigens was induced in nearly all NMRI mice and NOD-SCID mice vaccinated by temperature induced necrotic cell lysate (tab. 2 and 3). An IgG immune response against TF and Tn carbohydrate antigen is unusual because immunisation of mice by TF-antigen usually induces an IgM immune response. This might indicate that activation of the immune response by temperature-induced cell lysates is superior immunisation process involving a switch of antibody class associated with a T helper cell immune response as well as induction of memory immune responses against the above antigens. A specific human IgG immune response was induced in a murine immune system as well as in an implantated human immune system. Clearly cell lysates of necrotic cells induced a stronger specific humoral immune response than cell lysates of apoptotic cells. Cell lysates of tumor cells with increased HSP 70 expression (temperature induction at 41.2° C.) did not induced a specific humoral immune response in either mouse model (tab. 2 and 3). These are not in accordance with results of other authors (Dressel (2000), loc cit.; Feng (2001), loc. Cit.; Melcher, (1998), loc. cit.; Todryk (2000), loc. cit.) who described a strong immune response induced by cells with increased HSP 70 expression. Cell lysates of untreated tumor cells induced only poor specific humoral immune responses.

The invention claimed is:

1. A lysate obtainable by a process comprising the steps:
   (a) inducing necrosis of NM-F9 tumor cells (Accession No. DSM ACC 2606) or NM-D4 tumor cells (Accession No. DSM ACC 2605) by subjecting the cells to a temperature of more than 41.2° C. for at least 15 minutes; and
   (b) lysing said necrotic tumor cells to obtain a lysate that is capable of inducing a humoral immune response against the TF antigen.
2. Isolated dendritic cells loaded with lysate of claim 1.
3. A composition comprising the lysate of claim 1.
4. A composition comprising the dendritic cells of claim 2.
5. A vaccine comprising the lysate of claim 1.
6. A vaccine comprising the dendritic cells of claim 2.
7. The dendritic cells of claim 2, wherein said dendritic cells are immature.
8. The dendritic cells of claim 2, wherein said dendritic cells are mature.
9. The lysate of claim 1, wherein induction of necrosis is achieved by incubating said tumor cells at a temperature in the range of 45° C. to 55° C.
10. The dendritic cells of claim 2, wherein induction of necrosis is achieved by incubating said tumor cells at a temperature in the range of 45° C. to 55° C.
11. The lysate of claim 1, wherein induction of necrosis is achieved by incubating said tumor cells at a temperature in the range of 45.5° C. to 47° C.
12. The dendritic cells of claim 2, wherein induction of necrosis is achieved by incubating said tumor cells at a temperature in the range of 45.5° C. to 47° C.
13. The lysate of claim 1, wherein the induction of necrosis is performed in the range of 2 to 3 hours.
14. The dendritic cells of claim 2, wherein the induction of necrosis is performed in the range of 2 to 3 hours.
15. The lysate of claim 1, wherein more than 40% of the tumor cells are necrotic after induction of necrosis.
16. The dendritic cells of claim 2, wherein more than 40% of the tumor cells are necrotic after induction of necrosis.
17. The lysate of claim 1, wherein more than 70% of the tumor cells are necrotic after induction of necrosis.
18. The dendritic cells of claim 2, wherein more than 70% of the tumor cells are necrotic after induction of necrosis.
19. The lysate of claim 1, wherein the tumor cells are genetically engineered, mutated or infected by oncogenic viruses.
20. The dendritic cells of claim 2, wherein the tumor cells are genetically engineered, mutated or infected by oncogenic viruses.
21. The lysate of claim 1, wherein less than 33% of said tumor cells express membrane-bound HSP 70 protein and at least 16% of said tumor cells are necrotic after the cells are subjected to a temperature of more than 41.2° C. for at least 15 minutes.
22. The lysate of claim 1, wherein the induction of necrosis is performed in the range of 2 to 24 hours.
23. The lysate of claim 1, wherein:
   (a) after the cells are subjected to a temperature of more than 41.2° C. for at least 15 minutes, fewer tumor cells are positive for membrane-bound HSP 70 protein than tumor cells treated at a temperature of 41.2° C. or lower; and
   (b) more tumor cells are necrotic after the cells are subjected to a temperature of more than 41.2° C. for at least 15 minutes than cells subjected to a temperature of 41.2° C. or lower.
24. The lysate of claim 1, wherein:
   (a) after the cells are subjected to a temperature of 45° C. to 55° C. for at least 15 minutes, fewer tumor cells are positive for membrane-bound HSP 70 protein than tumor cells treated at a temperature lower than 45° C. or higher than 55° C.; and
   (b) more tumor cells are necrotic after the cells are subjected to a temperature of 45° C. to 55° C. for at least 15 minutes than cells subjected to a temperature of lower than 45° C. or higher than 55° C.
25. The lysate of claim 1, wherein:
   (a) after the cells are subjected to a temperature of 45° C. to 47.5° C. for at least 15 minutes, fewer tumor cells are positive for membrane-bound HSP 70 protein than tumor cells treated at a temperature lower than 45° C. or higher than 47.5° C.; and
   (b) more tumor cells are necrotic after the cells are subjected to a temperature of 45° C. to 47.5° C. for at least 15 minutes than cells subjected to a temperature of lower than 45° C. or higher than 47.5° C.
26. The dendritic cells of claim 2, wherein the induction of necrosis is performed in the range of 2 to 24 hours.
27. The lysate of claim 9, wherein less than 33% of said tumor cells express membrane-bound HSP 70 protein and at least 16% of said tumor cells are necrotic after the cells are subjected to a temperature in the range of 45° C. to 55° C. for at least 15 minutes.
28. The dendritic cells of claim 10, wherein less than 33% of said tumor cells express membrane-bound HSP 70 protein and at least 16% of said tumor cells are necrotic after the tumor cells are subjected to a temperature in the range of 45° C. to 55° C. for at least 15 minutes.
29. The lysate of claim 11, wherein less than 33% of said tumor cells express membrane-bound HSP 70 protein and at least 16% of said tumor cells are necrotic after the cells are subjected to a temperature in the range of 45.5° C. to 47° C. for at least 15 minutes.
30. The dendritic cells of claim 12, wherein less than 33% of said tumor cells express membrane-bound HSP 70 protein and at least 16% of said tumor cells are necrotic after the tumor cells are subjected to a temperature in the range of 45.5° C. to 47° C. for at least 15 minutes.
31. The lysate of claim 15, wherein less than 33% of said tumor cells express membrane-bound HSP 70 protein after the cells are subjected to a temperature of more than 41.2° C. for at least 15 minutes.
32. The lysate of claim 17, wherein less than 33% of said tumor cells express membrane-bound HSP 70 protein after the cells are subjected to a temperature of more than 41.2° C. for at least 15 minutes.

33. The dendritic cells of claim 16, wherein less than 33% of said tumor cells express membrane-bound HSP 70 protein after the tumor cells are subjected to a temperature of more than 41.2° C. for at least 15 minutes.

34. The dendritic cells of claim 18, wherein less than 33% of said tumor cells express membrane-bound HSP 70 protein after the tumor cells are subjected to a temperature of more than 41.2° C. for at least 15 minutes.

35. A lysate obtainable by a process comprising the steps:
   (a) inducing necrosis of NM-F9 tumor cells (Accession No. DSM ACC 2606) or NM-D4 tumor cells (Accession No. DSM ACC 2605) by subjecting the cells to a temperature of 42.4° C. or higher for at least 15 minutes; and
   (b) lysing said necrotic tumor cells to obtain a lysate that is capable of inducing a humoral immune response against the TF antigen.

36. The lysate of claim 35, wherein less than 33% of said tumor cells express membrane-bound HSP 70 protein and at least 16% of said tumor cells are necrotic after the cells are subjected to a temperature of 42.4° C. or higher for at least 15 minutes.

37. Isolated dendritic cells loaded with the lysate of claim 35.

38. The dendritic cells of claim 37, wherein less than 33% of said tumor cells express membrane-bound HSP 70 protein and at least 16% of said tumor cells are necrotic after the tumor cells are subjected to a temperature of 42.4° C. or higher for at least 15 minutes.

39. The lysate of claim 35, wherein:
   (a) after the cells are subjected to a temperature of 42.4° C. or higher for at least 15 minutes, fewer tumor cells are positive for membrane-bound HSP 70 protein than tumor cells treated at a temperature lower than 42.4° C.; and
   (b) more tumor cells are necrotic after the cells are subjected to a temperature of 42.4° C. or higher for at least 15 minutes than cells subjected to a temperature lower than 42.4° C.

* * * * *

UNITED STATES PATENT AND TRADEMARK OFFICE
CERTIFICATE OF CORRECTION

PATENT NO. : 7,595,192 B2
APPLICATION NO. : 10/524738
DATED : September 29, 2009
INVENTOR(S) : Steffen Goletz, Hans Baumeister and Ute Schöber It is certified that error appears in the above-identified patent and that said Letters Patent is hereby corrected as shown below:

On the Title page, item (73), the Assignee reads: "Glycotype GmbH", and should read -- Glycotope GmbH --.

IN THE CLAIMS:

In claim 1, column 33, line 24, change "41.2° C." to -- 41.2° C --.

In claim 2, column 33, line 29, change "with lysate" to -- with the lysate --.

In claim 9, column 33, line 40, change "45° C." to -- 45° C --.

In claim 10, column 33, line 43, change "45° C." to -- 45° C --.

In claim 11, column 33, line 46, change "45.5° C." to -- 45.5° C --.

In claim 12, column 33, line 49, change "45.5° C." to -- 45.5° C --.

In claim 21, column 34, line 4, change "41.2° C." to -- 41.2° C --.

In claim 23(a), column 34, line 10, change "41.2° C." to -- 41.2° C --.

In claim 23(a), column 34, line 12, change "41.2° C." to -- 41.2° C --.

In claim 23(b), column 34, line 15, change "41.2° C." to -- 41.2° C --.

In claim 23(b), column 34, line 17, change "C." to -- C --.

In claim 24(a), column 34, line 19, change "45° C." to -- 45° C --.

In claim 24(a), column 34, line 20, change "55° C." to -- 55° C --.

In claim 24(a), column 34, line 22, change "45° C." to -- 45° C --.

In claim 24(a), column 34, line 23, change "55° C.;" to -- 55° C; --.

In claim 24(b), column 34, line 25, change "45° C. to 55° C." to -- 45° C to 55° C --.

In claim 24(b), column 34, line 27, change "45° C." to -- 45° C --.

In claim 25(a), column 34, line 29, change "45° C." to -- 45° C --.

CERTIFICATE OF CORRECTION (continued)
U.S. Pat. No. 7,595,192 B2

In claim 25(a), column 34, line 30, change "47.5° C." to -- 47.5° C --.

In claim 25(a), column 34, line 32, change "45° C." to -- 45° C --.

In claim 25(a), column 34, line 33, change "47.5° C.;" to -- 47.5° C; --.

In claim 25(b), column 34, line 35, change "45° C. to 47.5° C." to -- 45° C to 47.5° C --.

In claim 25(b), column 34, line 37, change "45° C." to -- 45° C --.

In claim 27, column 34, line 43, change "45° C. to 55° C." to -- 45° C to 55° C --.

In claim 28, column 34, line 49, change "C. to 55° C." to -- C to 55° C --.

In claim 29, column 34, line 53, change "45.5° C. to 47° C.," to -- 45.5° C to 47° C, --.

In claim 30, column 34, line 59, change "45.5° C. to 47° C." to -- 45.5° C to 47° C --.

In claim 31, column 34, line 62, change "41.2° C." to -- 41.2° C --.

In claim 32, column 34, line 66, change "41.2° C." to -- 41.2° C --.

In claim 33, column 35, line 4, change "41.2° C." to -- 41.2° C --.

In claim 34, column 35, line 8, change "41.2° C." to -- 41.2° C --.

In claim 35(a), column 35, line 13, change "42.4° C." to -- 42.4° C --.

In claim 36, column 35, line 20, change "42.4° C." to -- 42.4° C --.

In claim 38, column 36, line 6, change "42.4° C." to -- 42.4° C --.

In claim 39(a), column 36, line 9, change "42.4° C." to -- 42.4° C --.

In claim 39(a), column 36, line 12, change "42.4° C.;" to -- 42.4° C; --.

In claim 39(b), column 36, line 15, change "42.4° C." to -- 42.4° C --.

Signed and Sealed this

Twenty-sixth Day of January, 2010

David J. Kappos
*Director of the United States Patent and Trademark Office*